(12) United States Patent
Shtyrlin et al.

(10) Patent No.: US 10,759,810 B2
(45) Date of Patent: Sep. 1, 2020

(54) ANTIBACTERIAL AGENTS BASED ON CIPROFLOXACIN DERIVATIVES

(71) Applicants: AO "TATKHIMFARMPREPARATY", Kazan (RU); Kazan Federal University, Kazan (RU)

(72) Inventors: Yurij G. Shtyrlin, Kazan (RU); Nikita V. Shtyrlin, Kazan (RU); Mikhail V. Pugachev, Ul'yanovsk (RU); Roman S. Pavel'Ev, Kazan (RU); Al'fiya G. Iksanova, Kazan (RU); Elena V. Nikitina, Kazan (RU); Mikhail S. Dzyurkevich, Kaliningrad Obl. (RU)

(73) Assignees: AO "Tatkhimfarmpreparaty", Kazan (RU); Kazan Federal University, Kazan (RU)

( * ) Notice: Subject to any disclaimer, the term of this patent is extended or adjusted under 35 U.S.C. 154(b) by 0 days.

(21) Appl. No.: 16/397,860

(22) Filed: Apr. 29, 2019

(65) Prior Publication Data

US 2019/0248802 A1 Aug. 15, 2019

Related U.S. Application Data

(63) Continuation of application No. PCT/RU2017/000807, filed on Oct. 31, 2017.

(30) Foreign Application Priority Data

Nov. 2, 2016 (RU) .................................. 2016143072

(51) Int. Cl.
C07D 491/056 (2006.01)
C07D 401/14 (2006.01)
(52) U.S. Cl.
CPC ....... C07D 491/056 (2013.01); C07D 401/14 (2013.01)
(58) Field of Classification Search
CPC ... A61K 31/496; C07D 401/14; C07D 493/04
(Continued)

(56) References Cited

U.S. PATENT DOCUMENTS

| | | | |
|---|---|---|---|
| 4,620,007 | A | 10/1986 | Grohe et al. |
| 2002/0169168 | A1 | 11/2002 | Streuff et al. |
| 2003/0181719 | A1 | 9/2003 | Zhi et al. |

FOREIGN PATENT DOCUMENTS

| | | |
|---|---|---|
| RU | 2193558 C2 | 11/2002 |
| RU | 2248970 C2 | 3/2005 |

(Continued)

OTHER PUBLICATIONS

International Search Report from PCT/RU2017/000807, dated Oct. 31, 2017, dated Jan. 18, 2018.

(Continued)

*Primary Examiner* — Jeffrey H Murray
(74) *Attorney, Agent, or Firm* — Patentbar International, P.C.

(57) ABSTRACT

New derivatives of ciprofloxacin of the general formula (I) show antibacterial properties. The compounds can be used in medicine and veterinary.

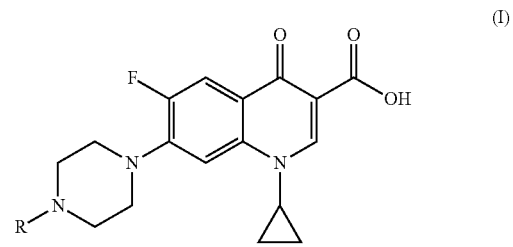

where R=

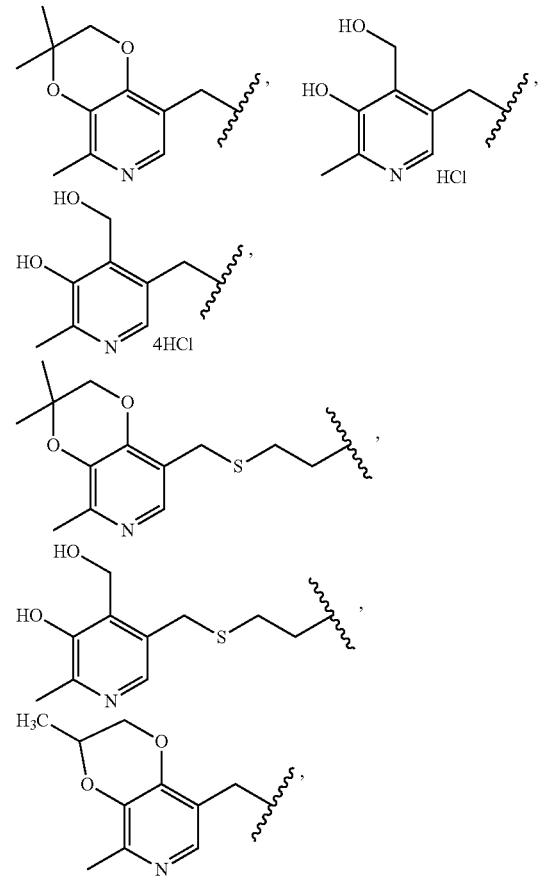

(Continued)

-continued

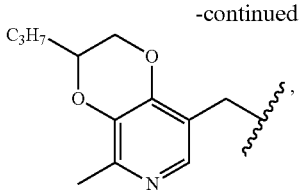

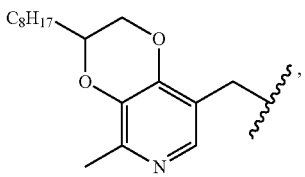

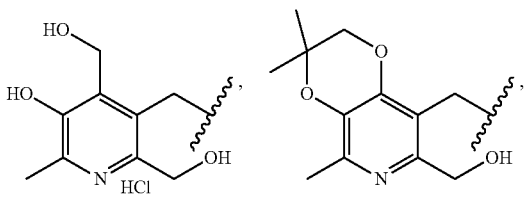

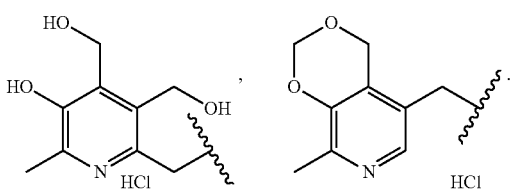

1 Claim, No Drawings

(58) Field of Classification Search
USPC .................................. 514/253.08; 544/363
See application file for complete search history.

(56) References Cited

FOREIGN PATENT DOCUMENTS

RU 2466728 C1 11/2012
WO 2011/034971 A1 3/2011

OTHER PUBLICATIONS

Sárkoezy G., Quinolones: a class of antimicrobial agents, Vet. Med. Czech, 2001, pp. 257-274, v. 46 (9-10).
Lowy F.D., Antimicrobial resistance: the example of *Staphylococcus aureus*, The Journal of Clinical Investigation, May 2003, pp. 1265-1273, v. 111, No. 9.
Emami, S. et al, Quinolones: Recent Structural and Clinical Developments, Iranian Journal of Pharmaceutical Research, 2005, pp. 123-136, v. 3.
Norrby S.R. Side-effects of quinolones: comparisons between quinolones and other antibiotics, Eur. J. Clin. Microbiol. Infect. Dis., 1991, pp. 378-383, v. 10, No. 4.
German, N. et al., Synthesis and evaluation of fluoroquinolone derivatives as substrate-based inhibitors of bacterial efflux pumps, European Journal of Medicinal Chemistry, 2008 pp. 2453-2463, v. 43.
Pokrovskaya, V. et al, Design, Synthesis, and Evaluation of Novel Fluoroquinolone-Aminoglycoside Hybrid Antibiotics, J. Med. Chem., 2009, pp. 2243-2254, v. 52.
Tomita I. et al, Synthesis of vitamin B6 derivatives. II. 3-Hydroxy-4-hydroxymethyl-2-methyl-5-pyridine acetic acid and related substances, Department of Biochemistry and Biophysics, Iowa State University, Jun. 1966, pp. 178-183, v. 3.
Serwa, R. et al, Preparation and Investigation of Vitamin B6-Derived Aminopyridinol Antioxidants, Chem. Eur. J., 2010, pp. 14106-14114, v. 16.
Pugachev, M.V. et. al, Synthesis and antibacterial activity of novel phosphonium salts on the basis of pyridoxine, Bioorganic & Medicinal Chemistry, 2013, pp. 4388-4395, v. 21.
Pugachev, M.V. et al, Bis-phosphonium salts of pyridoxine: the relationship between structure and antibacterial activity Elioorganic & Medicinal Chemistry, 2013, pp. 7330-7342, v. 21.
Beloborodova, N. V. et al, Fluoroquinolones in pediatrics—for and against, Pediatrics, 1996, No. 2, pp. 76-84.
Chen Yeh-Long et al., Synthesis and antimycrobacterial evaluation of pyranone and pyridinone metal-chelator bearing fluoroquinolones, The Chinese Pharmaceutical Jounmal, 2005, pp. 57-70, v. 57, No. 2-6.
Yakovlev, S. V., Antibacterial Drugs of the Fluorhinolone Group, Regular Issues of the "RMJ," Nov. 4, 1997, p. 5, No. 21.

ANTIBACTERIAL AGENTS BASED ON CIPROFLOXACIN DERIVATIVES

RELATED APPLICATIONS

This Application is a Continuation application of International Application PCT/RU2017/000807, filed on Oct. 31, 2017, which in turn claims priority to Russian Patent Application RU2016143072, filed Nov. 2, 2016, both of which are incorporated herein by reference in their entirety.

FIELD OF THE INVENTION

The invention related to the chemistry of organic heterocyclic compounds, namely, to the new derivatives of ciprofloxacin of the general formula (I) exhibiting antibacterial properties. Compounds can be used in medicine and veterinary medicine.

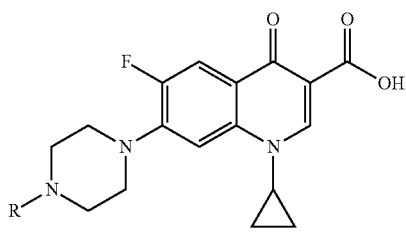

(I)

where R=

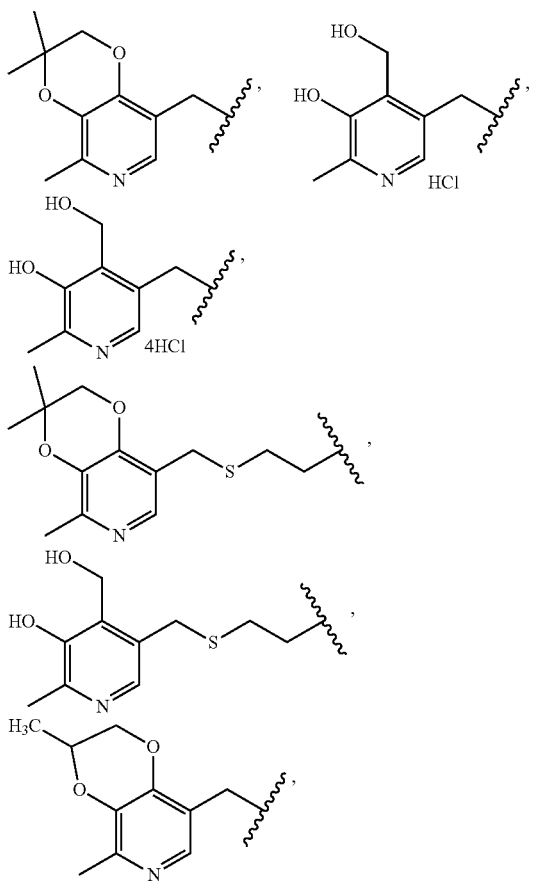

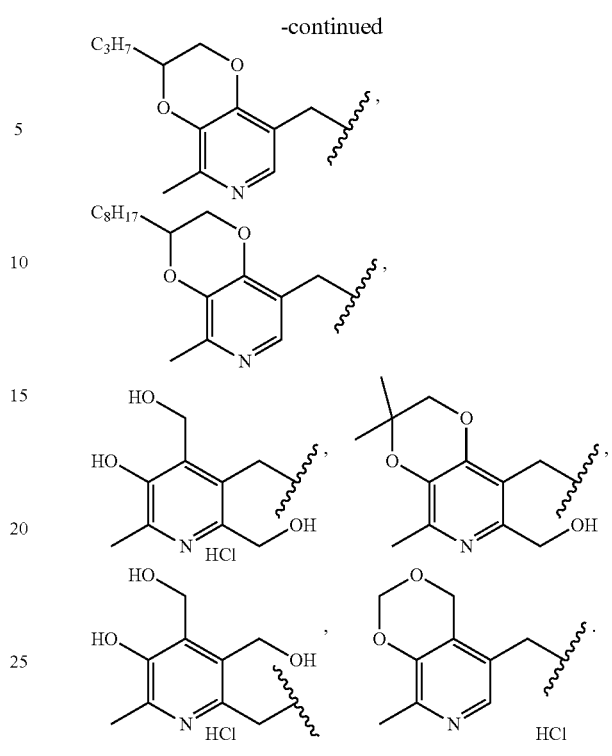

BACKGROUND OF THE INVENTION

Search and directed synthesis of highly effective and safe antibacterial agents is one of the primary tasks of modern pharmacology and medical chemistry. In recent years there has been a marked increase in the number and prevalence of infectious diseases caused by the emergence of new highly pathogenic strains of microorganisms and an increase in their resistance to existing antibiotics.

Despite the presence of episodically occurring acute bacterial infections, for example, caused by mutated strains of *Escherichia coli* (O104: H4), one of the main causes of death in developed countries remain well-known bacteria—*Staphylococcus aureus, Escherichia coli* and *Pseudomonas aeruginosa*.

In particular, according to the WHO, *Staphylococcus aureus* tops the list of bacteria that are most frequently cause infection in medical institutions. Methicillin-resistant strains of *Staphylococcus aureus*, which cause sepsis and severe forms of skin and soft tissue infections (furunculosis, phlegmon, scalded skin syndrome), are a particular danger to humans, causing up to 31% of patients to die.

One of the most effective antibacterial preparations used in modern practice for the suppression of methicillin-resistant strains of *Staphylococcus aureus* are fluoroquinolone preparations, in particular, ciprofloxacin. According to the chemical structure, ciprofloxacin is a fluoroquinolone derivative.

The mechanism of its action is to suppress bacterial DNA gyrase (topoisomerase II and IV, responsible for the supercoiling of chromosomal DNA around nuclear RNA, which is necessary for reading genetic information), impair DNA synthesis, growth and division of bacteria, which causes pronounced morphological changes (including in cell wall and membranes) and rapid death of a bacterial cell.

Ciprofloxacin has an antibacterial effect with the greatest activity against a number of aerobic gram-negative and gram-positive bacteria, namely: *Pseudomonas aeruginosa, Haemophilus influenzae, Escherichia coli, Shigella* spp., *Salmonella* spp., *Neisseria meningitidis, N. Gonorrhoeae, Staphylococcus* spp. (producing and not producing penicillinase), some strains of *Enterococcus* spp., as well as *Campylobacter* spp., *Legionella* spp., *Mycoplasma* spp., *Chlamidia* spp., *Mycobacterium* spp [Yakovlev V. P. *Antibacterialnye preparaty gruppy ftorchinolov [Antibacterial drugs of the fluoroquinolone group]/Rus. med. journal*—1997, Vol. 0.5—p. 1405-1413.].

Ciprofloxacin is used in infectious and inflammatory diseases caused by microorganisms susceptible to ciprofloxacin, including diseases of the respiratory tract, abdominal cavity and organs of the pelvis, bones, joints, skin, septicemia, severe infections of ENT-organs, etc. [Sárközy G. *Quinolones: a class of antimicrobial agents/Vet. Med.*—2001—V. 46—P. 257-274].

A significant drawback of ciprofloxacin is the restriction of intake by age —prescription of this drug is contraindicated in children and adolescents, as it causes a growth disorder [Beloborodova N. V, Padeyskaya E. N., Biryukov A. V. *Ftorquinolony v pediatrii—za i protiv [Fluoroquinolones in pediatrics—pros and cons]/Pediatrics Publ.*—1996. Vol. 2.—P. 76-84.].

Also, the disadvantages of ciprofloxacin include quite common side effects of the drug—abdominal pain, nausea, dysbiosis, insomnia, dizziness, allergic reactions (angioedema, urticaria, pruritus). In recent years, there has been a significant increase in the resistance of microorganisms to the entire class of fluoroquinolones [Norrby S. R. *Side-effects of quinolones: comparisons between quinolones and other antibiotics/Eur. J. Clin. Microbiol. Infect. Dis.*—1991—V.10—P. 378-383].

As the effective filing date of the claimed invention it is known that most methicillin-resistant staphylococci are resistant to cyprofloxacin [Lowy F. D. *Antimicrobial resistance: the example of Staphylococcus aureus/J. Clin. Invest.*—2003—V. 111.—P. 1265-1273.].

The study of the relationships of structure-biological activity in a series of ciprofloxacin derivatives revealed that the nature of the substituent at the C-7 atom has the greatest influence on their biological action [Emamia S., Shafiee A., Foroumadi A. *Quinolones: Recent Structural and Clinical Developments/Iran. J. Pharm. Res.*—2005.—V.-P. 123-136].

The source [N. German, P. Wei, G. W. Kaatz and R. J. Kerns. *Synthesis and evaluation of fluoroquinolone derivatives as substrate-based inhibitors of bacterial efflux pumps/ Eur. J. Med. Chem.*—2008—V. 43. —P. 2453-2463] describes ciprofloxacin derivatives modified at the C-7 atom of the piperazine ring by fragments of various peptides and substituted diarylureas. These compounds showed slightly lower antibacterial activity compared to ciprofloxacin.

Modification of ciprofloxacin by the C-7 atom of the piperazine ring with an aminoglycoside antibiotic neomycin through a bridge containing a 1,2,3-triazole fragment resulted in hybrid structures exhibiting high antibacterial activity against strains of gram-negative and gram-positive bacteria [V. Pokrovskaya, V. Belakhov, M. Hainrichson, S. Yaron and T. Baasov *Design, Synthesis, and Evaluation of Novel Fluoroquinolone-Aminoglycoside Hybrid Antibiotics/ J. Med. Chem.*—2009—V. 5. P, 2243-2254].

An international application [WO2011034971A1. *Modified fluoroquinolone compounds and methods of using the samee/Designmedix, Inc.* —Publ. on Mar. 24, 2011] describes ciprofloxacin derivatives by the C-7 atom of the piperazine ring, significantly exceeding its antibacterial activity against strains of gram-positive and gram-negative bacteria.

It should be noted that a significant disadvantage of all the above compounds is their high toxicity, which does not allow them to be considered as candidates for antibacterial preparations.

SUMMARY OF THE INVENTION

The object of the present invention is to create new non-toxic (safe) antibacterial preparations of the fluoroquinolone series based on ciprofloxacin with high antibacterial activity, with the aim of expanding the arsenal of known means of the indicated purpose.

The technical result of the present invention is to obtain new compounds of general formula (I), containing both a fragment of a natural compound (pyridoxine, a member of the vitamin $B_6$ group), and a fragment of the antibacterial drug ciprofloxacin.

The problem is solved, and the specified technical result is achieved by obtaining the claimed new derivatives of ciprofloxacin of formula (I):

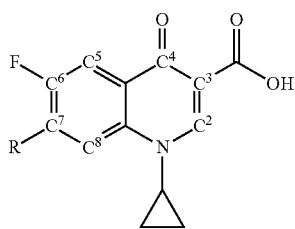

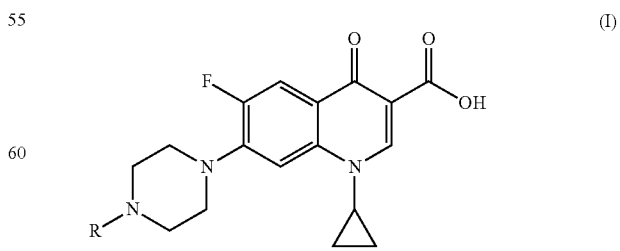

Most often, such substituents are five- and six-membered nitrogen-containing heterocycles, such as piperazine, pyrimidine, 1,2,3-triazole, pyrrolidine, and their substituted derivatives.

according to reaction sequences 1-7 below, where the claimed compounds are indicated by numbers I-1 to I-12.

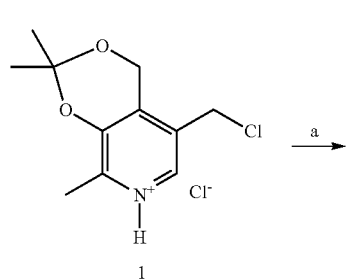
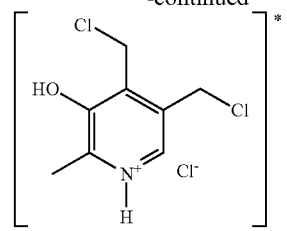
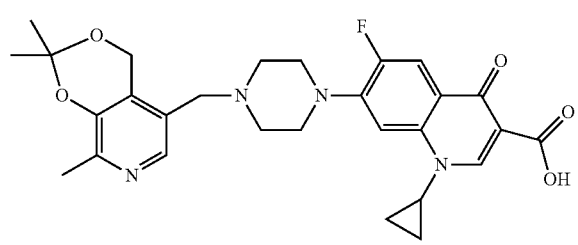
I-1
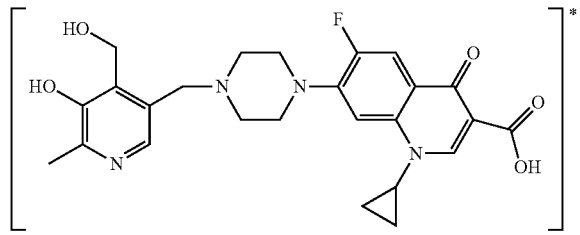
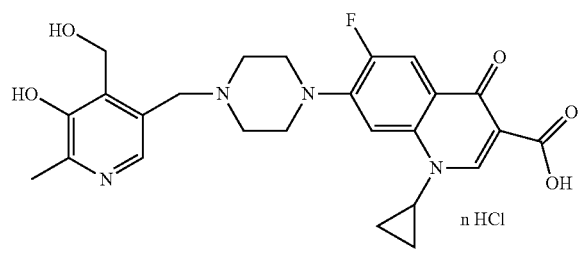
I-2 n = 1
I-3 n = 4
Reaction Sequence 1.
(a) N, N-Dimethylformamide (hereinafter DMFA), ciprofloxacin, KI, $NaHCO_3$, 20° C., 4 h.
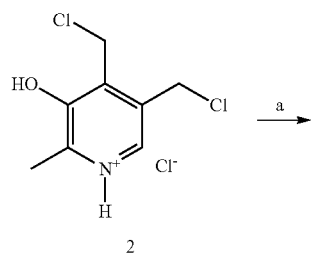
2
* [ ] indicates non-extricated intermediate products
Reaction Sequence 2.
(a) $H_2O$, 55° C., 3 h; (b) $H_2O$, DMFA, ciprofloxacin hydrochloride, KI, $NaHCO_3$, 55° C., 6 h; (c) $H_2O$, HCl.
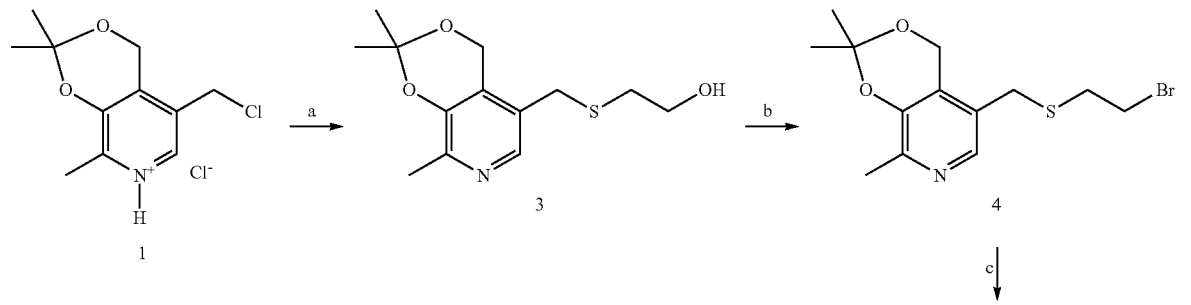
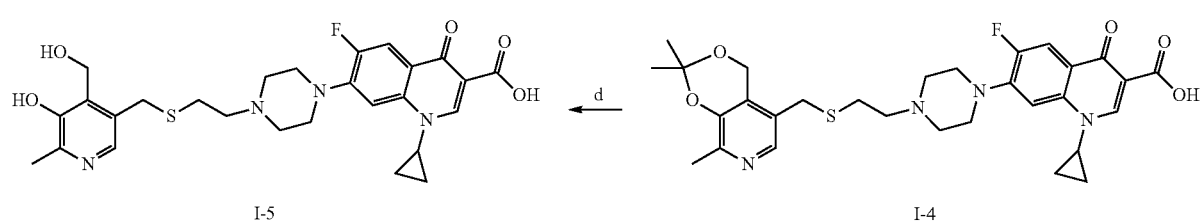
I-5          I-4

Reaction Sequence 3.

(a) CH₃OH, SHCH₂CH₂OH, CH₃ONa, 50° C., 5 h; (b) CHCl₃, NBS, PPh₃, 20° C., 1 h; (c) DMFA, ciprofloxacin, KI, NaHCO₃, 20° C., 4 h; (d) H₂O, HCl, 25° C., 24 h.

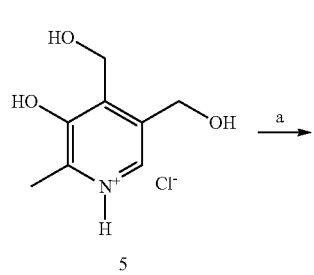

5

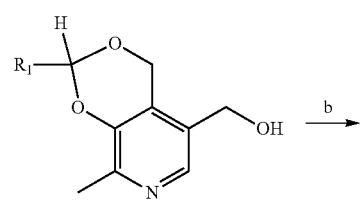

6. R₁ = CH₃
7. R₁ = C₃H₇
8. R₂ = C₈H₁₇

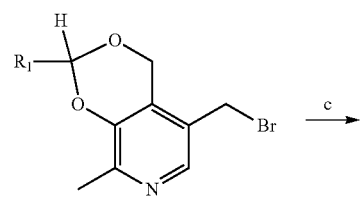

9. R₁ = CH₃
10. R₁ = C₃H₇
11. R₂ = C₈H₁₇

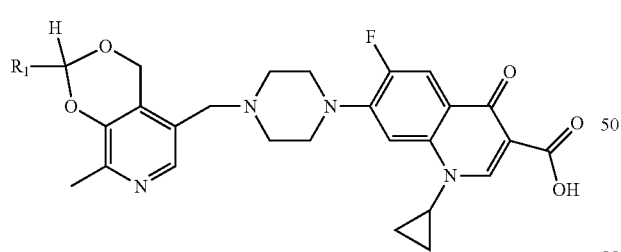

I-6. R₁ = CH₃
I-7. R₁ = C₃H₇
I-8. R₂ = C₈H₁₇

Reaction Sequence 4.

(a) CH₃C(O)H, HCl, 3-5° C., 3 h or C₆H₆, R₁C(O)H, p-TsOH, boiling, 8 h; (b) CHCl₃, NBS, PPh₃, 20° C., 1 h; (c) DMFA, ciprofloxacin, KI, NaHCO₃, 20° C., 4 h.

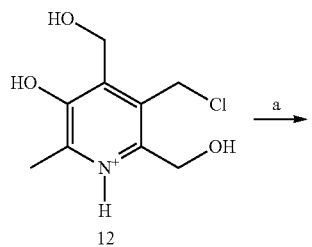

12

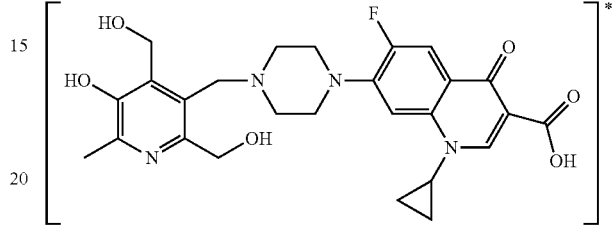

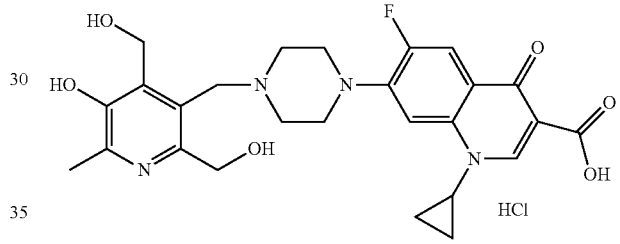

I-9

* [ ] indicates non-extricated intermediate product

Reaction Sequence 5.

(a) DMFA, ciprofloxacin, KI, NaHCO₃, 20° C., 4 h. (b) H₂O, HCl.

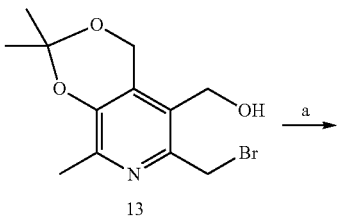

13

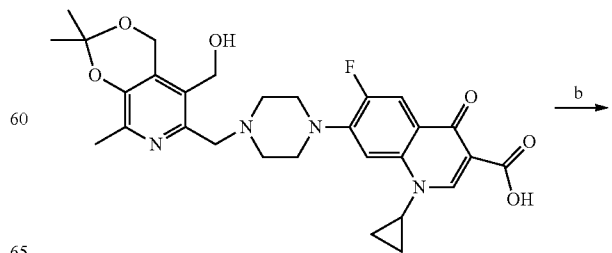

I-10

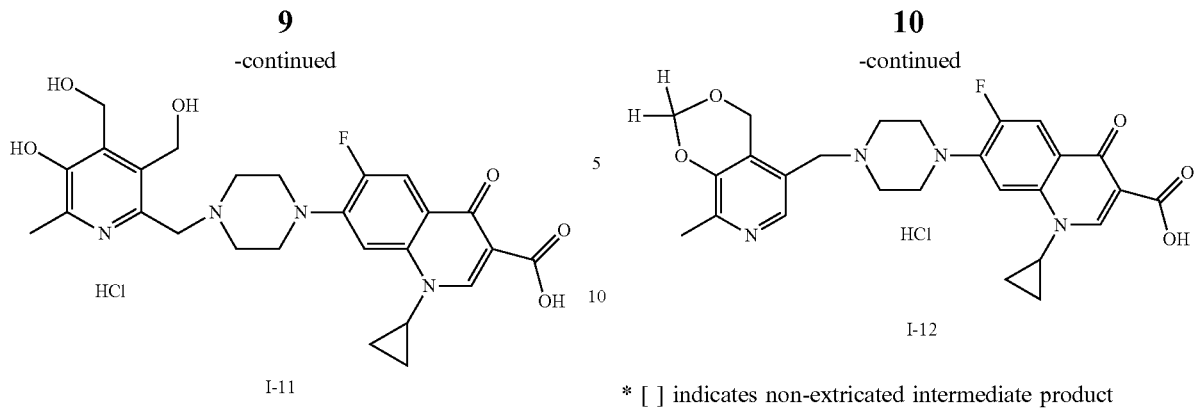

I-11

Reaction Sequence 6.

(a) ciprofloxacin, KI, NaHCO₃, 20° C., 4 h. (b) H₂O, HCl, 25° C., 24 h.

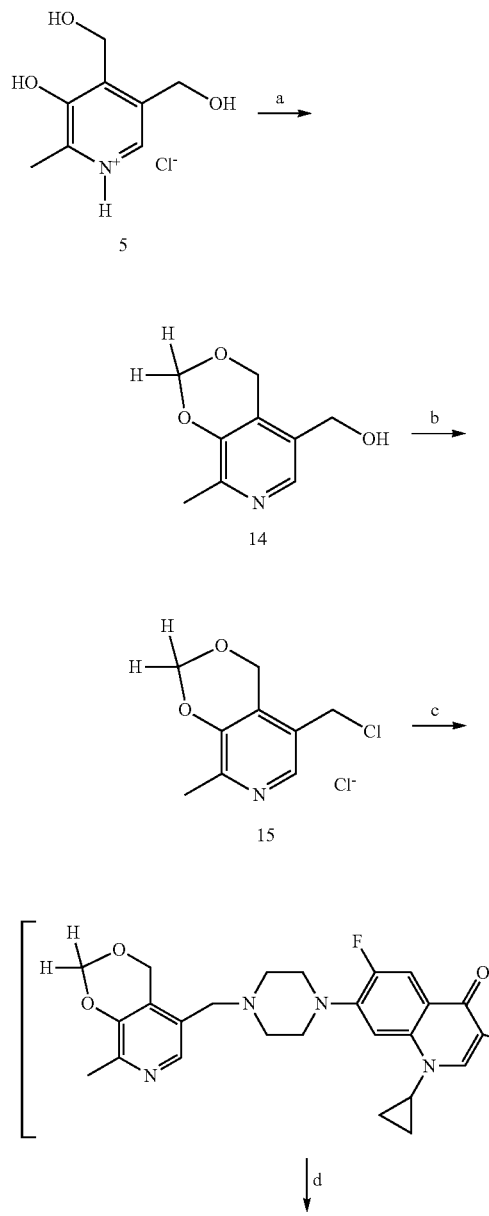

I-12

* [ ] indicates non-extricated intermediate product

Reaction Sequence 7.

(a) C₆H₆, paraform, p-TsOH, boiling, 6 h; (b) CHCl₃, SOCl₂, 20° C., 3 h;

(c) DMFA, ciprofloxacin, KI, NaHCO₃, 80° C., 4 h. (d) H₂O, HCl.

Characteristics of the new compounds obtained in accordance with reaction sequences 1-7, are given below in the examples of specific performance.

The structures of the compounds obtained were confirmed by mass spectrometry, $^1$H and $^{13}$C NMR spectroscopy.

NMR spectra are recorded on the Bruker AVANCE-400 device. The chemical shift is determined with respect to the signals of residual protons of deuterated solvents ($^1$H and $^{13}$C).

Melting temperatures are determined using Stanford Research Systems MPA-100 OptiMelt. Control over the course of reactions and purity of compounds is carried out by TLC method on Sorbfil Plates.

MALDI mass spectra are recorded on Bruker's Ultraflex III instrument equipped with solid state laser and time-of-flight mass analyzer. Accelerating voltage is 25 kV. The samples are applied to the Anchor Chip target. Spectra recording is performed in the mode of positive ions. The resulting spectrum is the sum of 300 spectra obtained at different points of the sample. As matrices are used 2,5-dihydroxybenzoic acid (DHB) (Acros, 99%) and p-nitroaniline (PNA). Chloroform is used for the preparation of matrices. Application of samples on the target is performed by the method of "dried drops".

DETAILED DESCRIPTION OF THE PREFERRED EMBODIMENTS

Examples of Specific Implementation of the Invention

Example 1. Preparation of hydrochloride of 1-cyclopropyl-6-fluoro-7-(4-((2,2,8-trimethyl-4H-[1,3]dioxino-[4,5-c]pyridine-5-yl) methyl) piperazinyl)-4-oxo-1,4-dihydroquinolin-3-carboxylic acid (I-1)

To a solution of 1.44 g (5.5 mmol) of compound (1) [Tomita I., Brooks H G., Metzler D. E. *Synthesis of vitamin B₆ derivatives. II. 3-Hydroxy-4-hydroxymethyl-2-methyl-5-pyridine acetic acid and related substances/J. Heterocycl. Chem.*—1966—V.3., N.2.—P. 178-183] in 20 ml of absolute DMFA at 20° C. are added successively 1.50 g (4.5 mmol) of ciprofloxacin, 0.84 g (10.0 mmol) of sodium bicarbonate and 0.23 g (1.4 mmol) of potassium iodide. After 4 h the solvent is removed in a vacuum. The dry residue is extracted with ethyl acetate, the insoluble part is filtered out, and the filtrate is dried to dryness and recrystallized from a mixture of solvents acetone:water=2:1. Yield is 1.12 g (47%), light yellow crystals, melting temperature is 243° C. (decomp.).

NMR spectrum $^1$H (400 MHz, CDCl$_3$) δ, ppm: 1.14-1.18 m (2H, cyclopropyl CH$_2$), 1.32-1.37 m (2H, cyclopropyl CH$_2$), 1.53 s (6H, 2CH$_3$), 2.36 s (3H, CH$_3$), 2.61 m (4H, piperazino 2CH$_2$), 3.29 m (4H, piperazino 2CH$_2$), 3.44 s (2H, CH$_2$N), 3.50-3.56 M (1H, cyclopropyl CH), 4.98 c (2H, CH$_2$O), 7.28 d (1H, $^4J_{H-F}$=7.1 Hz, CH$_{ar}$), 7.78 d (1H, $^3J_{H-F}$=13.1 Hz, CH$_{ar}$), 7.87 s (1H, CHO, 8.60 s (1H, CH$_{pyr}$), 14.95 br s (1H, OH).

NMR spectrum $^{13}$C (100 MHz, CDCl$_3$) δ, ppm.: 8.18 s (cyclopropyl 2CH$_2$), 18.43 s (CH$_3$), 24.74 s (2CH$_3$), 35.36 s (cyclopropyl CH), 49.79 d ($^4J_{C-F}$=4.7 Hz, piperazino 2CH$_2$), 52.55 s (piperazino 2 CH$_2$), 57.46 s (CH$_2$), 58.77 s (CH$_2$), 99.62 s (C(CH$_3$)$_2$), 104.86 s (C$_{ar}$), 107.78 s (CO), 112.00 d ($^2J_{C-F}$=23.5 Hz, C$_{ar}$), 119.42 d ($^3J_{C-F}$=7.8 Hz, C$_{ar}$), 126.32 (C$_{pyr}$), 126.48 s (C$_{pyr}$), 139.02 s (C), 140.42 s (C), 145.77 d ($^2J_{C-F}$=10.2 Hz, C$_{ar}$—N), 146.13 s (C), 147.26 s (C), 147.52 s (C), 153.57 d ($^1J_{C-F}$=251.6 Hz, C$_{ar}$—F), 166.86 s (C(O) OH), 176.83 d ($^4J_{C-F}$=2.2 Hz, C=O).

MALDI-MS: [M+H]$^+$ 523.

Example 2. Preparation of Hydrochloride of 1-cyclopropyl-6-fluoro-7-(4-((5-hydroxy-4-hydroxymethyl-6-methylpyridine-3-yl) methyl) piperazinyl)-4-oxo-1,4-dihydroquinolin-3-carboxylic acid (I-2)

Solution of 2.50 g (10.3 mmol) of 3-hydroxy-4,5-chloromethyl-2-methylpyridinium hydrochloride (2) [R. Serwa, T. G. Nam, L. Valgimigli, S. Culbertson, C. L. Rector, B. S. Jeong, D. A. Pratt, N. A. Porter. *Preparation and Investigation of Vitamin B$_6$-Derived Aminopyridinol Antioxidants/ Chem. Eur. J.*—2010—V.16., N46.—P. 14106-14114] in 25 ml of distilled water mix for 3 h at 55° C. To the resulting solution add 75 ml of dimethyl formamide, 3.60 g (9.8 mmol) of ciprofloxacin hydrochloride and 3.38 g (40.2 mmol) of sodium bicarbonate. At the end of active gas release (2 minutes) add 0.25 g (1.50 mmol) of potassium iodide. The resulting solution is mixed for 6 h at 55° C. At the end of mixing, the solvent is removed in a vacuum. To the dry residue add 100 ml of distilled water and boil for 30 minutes. The insoluble residue is filtered out in a vacuum.

The residue is transferred to a 100 ml round bottom flask, 50 ml of distilled water is added and acidified with concentrated hydrochloric acid to pH=2.56. The solvent is removed in a vacuum.

The dry residue is transferred to a 100 ml round bottom flask, filled with 60 ml of water and neutralized while stirring by adding NaHCO$_3$ to pH=6.00. The precipitate is filtered out, transferred to a 100 ml round bottom flask, 50 ml of distilled water is added and acidified with concentrated hydrochloric acid to pH=2.56. The solution is dried in a vacuum. Yield is 2.75 g (54%), melting temperature is not lower than 190° C. (decomp.).

NMR spectrum $^1$H (400 MHz, DMSO-d$_6$) δ ppm: 1.19-1.20 m (2H, cyclopropyl CH$_2$), 1.30-1.32 m (2H, cyclopropyl CH$_2$), 2.64 s (3H, CH$_3$), 3.52 br s (4H, piperazino 2CH$_2$), 3.69-3.71 br s (4H, piperazino 2CH$_2$), 3.86 s (1H, cyclopropyl CH), 4.70 s (2H, CH$_2$), 4.96 s (2H, CH$_2$), 7.60 d (1H, $^4J_{H-F}$=7.3 Hz, CH$_{ar}$), 7.95 d (1H, $^3J_{H-F}$=13.0 Hz, CH$_{ar}$), 8.67 s (1H, CH), 8.72 s (1H, CH).

NMR spectrum $^{13}$C (100 MHz, DMSO-d$_6$), ppm: 7.66 s (cyclopropyl 2CH$_2$), 15.63 s (CH$_3$), 36.03 s (cyclopropyl CH), 46.32 s (piperazino 2CH$_2$), 50.71 s (piperazino 2 CH$_2$), 52.76 s (CH$_2$), 55.52 s (CH$_2$), 106.86 s (C$_{ar}$), 107.00 s (C$_{ar}$), 111.25 d ($^2J_{C-F}$=23.2 Hz, C$_{ar}$), 119.39 d ($^3J_{C-F}$=8.1 Hz, C$_{ar}$), 126.42 S (C$_{pyr}$), 135.37 S (C$_{pyr}$), 139.11 s (C), 143.70 d ($^2J_{C-F}$=10.4 Hz, C$_{ar}$—N), 144.01 s (C), 144.18 s (C), 148.30 s (C), 152.20 s (C), 152.88 d ($^1J_{C-F}$=248.9 Hz, C$_{ar}$F), 165.90 s (C(O) OH), 176.42 s (C=O).

MALDI-MS: [M-Cl]$^+$483.

Example 3. Preparation of tetrahydrochloride of 1-cyclopropyl-6-fluoro-7-(4-((5-hydroxy-4-hydroxymethyl-6-methylpyridine-3-yl) methyl) piperazinyl)-4-oxo-1,4-dihydroquinolin-3-carboxylic acid (1-3)

Solution of 2.50 g (10.3 mmol) of 3-hydroxy-4,5-chloromethyl-2-methylpyridinium hydrochloride (2) [R. Serwa, T. G. Nam, L. Valgimigli, S. Culbertson, C. L. Rector, B. S. Jeong, D. A. Pratt, N. A. Porter. *Preparation and Investigation of Vitamin B$_6$-Derived Aminopyridinol Antioxidants/ Chem. Eur. J.*—2010—V.16., N.46.—P. 14106-14114] in 25 ml of distilled water mix for 3 h at 55° C. To the resulting solution add 75 ml of dimethyl formamide, 3.60 g (9.8 mmol) of ciprofloxacin hydrochloride and 3.38 g (40.2 mmol) of sodium bicarbonate. At the end of active gas release 2 minutes) add 0.25 g (1.50 mmol) of potassium iodide. The resulting solution is mixed for 6 h at 55° C. At the end of mixing, the solvent is removed in a vacuum. To the dry residue add 100 ml of distilled water and boil for 30 minutes. The insoluble residue is filtered out in a vacuum.

The residue is transferred to a round bottom flask for 100 ml, and 50 ml of distilled water and 5 ml of concentrated hydrochloric acid are added. The solvent is removed in a vacuum. Yield is 4.23 g (65%), melting temperature is not lower than 220° C. (decomp.).

Evidence of the structure of tetrahydrochloride is carried out using the Argentometric titration method. The study is carried out on an automatic titrator Metrohm Basic Titrino 794 (dosing with an accuracy of 1 μl). Reagents: distilled water, silver nitrate AgNO$_3$, ≈1% solution of potassium chromate K$_2$CrO$_4$.

Preparation of the titrant solution: V$_k$=100 ml, m (AgNO$_3$)=1.70750 g, M$_r$ (AgNO$_3$)=169.87 g/mol, c (AgNO$_3$)=0.1005 M. After preparation, the dosing device of the titrator is filled up.

Preparation of sample solution: V$_k$=100 ml, m (sample)=0.49140 g, M$_r$ (1-3)=482.51 g/mol, M$_r$ (HCl)=36.46 g/mol, co (H$_2$O)=8.16%, m (sample without water)=0.45130 g.

Titration procedure: titration is performed according to the Mohr method (direct argentometric titration in the presence of potassium chromate). An aliquot of the test solution (V$_{al}$=20 ml) is transferred to a glass, where the stirring rod is placed. The pH of the initial solution is about 2.2, it is adjusted to a value of 9.5 with a concentrated solution of KOH (at a pH of about 4 a precipitate is formed which dissolves at a pH of about 9). Then 4-5 drops of potassium chromate are added (the solution turns yellow), the dispenser spout is immersed and slow titration is performed. First, silver chloride precipitate appears in the solution and the solution turns lemon-yellow. Then, when the titrant is added, a red precipitate of silver chromate appears, which, with stirring, gives an orange coloration, which disappears with time (at first quickly, but as it approaches the equivalence point more slowly). The end of the titration is determined by the orange color, non-fading within 2-3 minutes.

Titration results: the volume of titrant ($V_{titrant}$) according to the results of four measurements is: 5.898 ml, 5.828 ml, 5.752 ml and 5.807 ml.

$V_{average}$=5.821±0.060 ml $c$(HCl)=$c$(AgNO$_3$)*$V_{average}$/$V_{al.}$=0.02925±0.00030 M $v$(HCl)=$c$(HCl)*$V_k$=0.002925±0.000030 mol $m$(HCl)=$v$ (HCl)*$M_r$(HCl)=0.1066±0.0011 g $m$(I-3)=$m$(sample without water)−$m$(HCl) =0.3447±0.0011 g $v$(I-3)=$m$(I-3)/$M_r$(I-3)=0.0007144±0.0000023 mol $n$(HCl)=$v$(HCl)/$v$(I-3)=4.094±0.042

Thus, the compound I-3 contains 4 molecules of hydrogen chloride.

NMR spectrum $^1$H (400 MHz, DMSO-d$_6$) δ ppm: 0.99-1.03 m (2H, cyclopropyl CH$_2$), 1.23-1.28 m (2H, cyclopropyl CH$_2$), 2.56 s (3H, CH$_3$), 3.52 br m (9H, piperazino 4CH$_2$+cyclopropyl CH), 4.61 s (2H, CH$_2$), 4.98 s (2H, CH$_2$), 7.26 d (1H, $^3J_{H-F}$=12.9 Hz, CH$_{ar}$), 7.30 d (1H, $^4J_{H-F}$=7.2 Hz, CH$_{ar}$), 8.30 s (1H, CH), 8.41 s (1H, CH).

NMR spectrum $^{13}$C (100 MHz, DMSO-d$_6$+D$_2$O) δ, ppm: 9.12 s (cyclopropyl 2CH$_2$), 16.83 s (CH$_3$), 37.75 s (cyclopropyl CH), 48.05 d ($^4J_{C-F}$=4.8 Hz, piperazino 2CH$_2$), 53.25 s (piperazino 2 CH$_2$), 56.42 s (CH$_2$), 58.20 s (CH$_2$), 107.23 s (C$_{ar}$), 108.26 s (C$_{ar}$), 112.30 d ($^2J_{C-F}$=22.9 Hz, C$_{ar}$), 120.34 d ($^3J_{C-F}$=8.4 Hz, C$_{ar}$), 127.49 s (C$_{pyr}$), 136.11 s (C$_{pyr}$), 140.46 s (C), 145.56 d ($^2J_{C-F}$=10.2 Hz, C$_{ar}$—N), 146.61 s (C), 147.40 s (C), 149.79 s (C), 154.17 s (C), 154.82 d ($^1J_{C-F}$=251.6 Hz, C$_{ar}$—F), 170.25 s (C(O)OH), 177.40 s (C=O).

MALDI-MS: [M-4Cl]$^+$483.

Example 4. Preparation of 1-cyclopropyl-6-fluoro-7-(4-(2-(((2,2,8-trimethyl-4H-[1,3]dioxino-[4,5-c]pyridine-5-yl) methyl) sulfanyl) ethyl) piperazinyl)-4-oxo-1,4-dihydroquinolin-3-carboxylic acid (I-4)

Phase 1. Preparation of 5-(((2-hydroxyethyl) sulfanyl) methyl)-2,2,8-trimethyl-4H-[1,3]dioxino [4,5-c] pyridine (3)

2.69 g (10.2 mmol) of the compound (1) [Tomita L, Brooks H. G., Metzler D. E. *Synthesis of vitamin B$_6$ derivatives. IL 3-Hydroxy-4-hydroxymethyl-2-methyl-5-pyridine acetic acid and related substances/J. Heterocycl. Chem.*— 1966—V.3., N2.—P. 178-183] are added to a solution of 0.52 g (22.4 mmol) of sodium in 10 ml of absolute methanol, then 1.14 g (14.6 mmol) of mercaptoethanol are added with cooling. The reaction mixture is stirred at 50° C. for 5 hours. The precipitate is filtered out, the solvent is removed in a vacuum. The dry residue is dissolved in a minimum amount of chloroform and purified by column chromatography (eluent is chloroform, then ethyl acetate). Yield is 1.74 g (64%), white crystals, melting temperature is 103-104° C.

NMR spectrum $^1$H (400 MHz, CDCl$_3$) δ, ppm: 1.53 s (6H, 2CH$_3$), 2.37 s (3H, CH$_3$), 2.61 t (2H, $^3J_{HH}$=6.1 Hz, SCH$_2$CH$_2$OH), 3.00 s (1H, OH), 3.58 s (2H, CH$_2$S), 3.71 t (2H, $^3J_{HH}$=6.1 Hz, SCH$_2$CH$_2$OH), 4.94 s (2H, CH$_2$O), 7.83 s (1H, CH).

NMR spectrum $^{13}$C (100 MHz, CDCl$_3$) δ, ppm.: 18.42 s (CH$_3$), 24.82 s (2CH$_3$), 30.07 s (SCH$_2$CH$_2$OH), 34.44 s (CH$_2$S), 58.52 s (CH$_2$O), 60.09 s (CH$_2$O), 99.91 s (C(CH$_3$)$_2$), 125.63 s (C$_{pyr}$), 126.63 s (C$_{pyr}$), 139.93 s (C$_{pyr}$), 146.46 s (C$_{pyr}$), 147.46 s (C$_{pyr}$).

Phase 2. Preparation of 5-(((2-bromoethyl) sulfanyl) methyl)-2,2,8-trimethyl-4H-[1,3]dioxino [4,5-c] pyridine (4)

1.70 g (6.5 mmol) of triphenylphosphine and 1.16 g (6.5 mmol) of bromosuccinimide are added to a solution of 1.74 g (6.5 mmol) of compound (3) in 20 ml of absolute chloroform at 20° C. After 1 h, the solution is concentrated in a vacuum and purified by column chromatography (eluent: diethyl ether:petroleum ether=2:1). Yield is 1.42 g (66%), light brown oil.

NMR spectrum $^1$H (400 MHz, CDCl$_3$) δ, ppm: 1.54 s (6H, 2CH$_3$), 2.39 s (3H, CH$_3$), 2.86 t (2H, $^3J_{HH}$=7.6 Hz, SCH$_2$CH$_2$Br), 3.40 t (2H, $^3J_{HH}$=7.6 Hz, SCH$_2$CH$_2$Br), 3.60 s (2H, CH$_2$S), 4.93 s (2H, CH$_2$O), 7.85 s (1H, CH).

NMR spectrum $^{13}$C (100 MHz, CDCl$_3$) δ, ppm.: 18.60 s (CH$_3$), 24.85 s (2CH$_3$), 30.18 s (SCH$_2$CH$_2$Br), 30.57 s (SCH$_2$CH$_2$Br), 33.69 s (CH$_2$S), 58.52 s (CH$_2$O), 99.96 s (C(CH$_3$)$_2$), 125.41 s (C$_{pyr}$), 126.15 s (C$_{pyr}$), 139.89 s (C$_{pyr}$), 146.48 s (C$_{pyr}$), 147.92 s (C$_{pyr}$).

Phase 3. Preparation of 1-cyclopropyl-6-fluoro-7-(4-(2-(((2,2,8-trimethyl-4H-[1,3]dioxino-[4,5-c]pyridine-5-yl) methyl) sulfanyl) ethyl) piperazinyl)-4-oxo-1,4-dihydroquinolin-3-carboxylic acid (I-4)

0.46 g (1.4 mmol) of ciprofloxacin, 0.12 g (1.4 mmol) of sodium bicarbonate and 0.05 g (0.4 mmol) of potassium iodide are added successively to a solution of 0.49 g (1.5 mmol) of compound (4) in 20 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. Yield is 0.41 g (51%), light yellow crystals, melting temperature is 206-208° C. (decomp.).

NMR spectrum $^1$H (400 MHz, CDCl$_3$) δ, ppm: 1.16-1.20 m (2H, cyclopropyl CH$_2$), 1.35-1.40 m (2H, cyclopropyl CH$_2$), 1.54 s (6H, 2CH$_3$), 2.38 s (3H, CH$_3$), 2.60-2.62 m (4H, piperazino 2CH$_2$), 2.64-2.67 m (4H, SCH$_2$CH$_2$N), 3.31-3.33 m (4H, piperazino 2CH$_2$), 3.51-3.56 m (1H, cyclopropyl CH), 3.59 s (2H, CH$_2$N), 4.96 s (2H, CH$_2$O), 7.32 d (1H, $^4J_{H-F}$=7.1 Hz, CH$_{ar}$), 7.85 S (1H, CH$_{ar}$), 7.93 d (1H, $^3J_{H-F}$=13.1 Hz, CH$_{ar}$), 8.70 s (1H, CH$_{pyr}$), 14.97 br s (1H, OH).

NMR spectrum $^{13}$C (100 MHz, CDCl$_3$) δ, ppm.: 8.33 s (cyclopropyl 2CH$_2$), 18.60 s (CH$_3$), 24.85 s (2CH$_3$), 28.75 s (CH$_2$), 30.57 s (CH$_2$), 35.40 s (cyclopropyl CH), 49.82 d ($^4J_{C-F}$=4.8 Hz, piperazino 2CH$_2$), 52.74 s (piperazino 2CH$_2$), 57.81 s (CH$_2$), 58.53 s (CH$_2$), 99.87 s (C(CH$_3$)$_2$), 104.91 d ($^4J_{C-F}$=3.0 Hz, C$_{ar}$), 108.16 s (C$_{ar}$), 112.41 d ($^2J_{C-F}$=23.5 Hz, C$_{ar}$), 119.84 d ($^3J_{C-F}$=7.7 Hz, C$_{ar}$), 125.42 s (C$_{pyr}$), 126.62 s (C$_{pyr}$), 139, 17 s (C), 140.04 s (C), 145.95 d ($^2J_{C-F}$=10.5 Hz, C$_{ar}$—N), 146.42 s (C), 147.46 s (C), 147.54 s (C), 153.77 d ($^1J_{C-F}$=251.6 Hz, C$_{ar}$—F), 167.08 s (C(O)OH), 177.16 s (C=O).

MALDI-MS: [M+H]$^+$ 583.

Example 5. Preparation of 1-cyclopropyl-6-fluoro-7-(4-(2-(((5-hydroxy-4-hydroxymethyl-6-methyl-pyridine-3-yl) methyl) sulfanyl) ethyl) piperazinyl)-4-oxo-1,4-dihydroquinolin-3-carboxylic acid (I-5)

0.24 g (0.4 mmol) of the ciprofloxacin derivative (I-4) and 1 ml of concentrated HCl in 20 ml of water are stirred for 24 h at 25° C. Then the solution is neutralized with sodium bicarbonate to pH=6. The precipitate is filtered out and washed successively with acetone, chloroform and water. Yield is 0.12 g (52%), light yellow crystals, melting temperature is 135-140° C. (decomp.).

NMR spectrum $^1$H (400 MHz, DMSO-d$_6$) δ ppm: 1.18 br s (2H, cyclopropyl CH$_2$), 1.32 br s (21-1, cyclopropyl CH$_2$), 2.32 s (3H, CH$_3$), 2.58-2.64 m (8H, piperazino2CH$_2$, SCH$_2$CH$_2$N), 3.32-3.36 m (4H, piperazino 2CH$_2$), 3.61-3.67 m (1H, cyclopropyl CH), 3.80 s (2H, CH$_2$N), 4.82 s (2H, CH$_2$O), 5.88 br s (1H, OH), 7.56 br s (1H CH$_{ar}$), 7.82 s (1H, CH$_{ar}$), 7.88 d (1H, $^3J_{H-F}$=13.2 Hz, CHO, 8.65 S (1H, CH$_{pyr}$), 9.32 br s (1H, OH).

NMR spectrum $^{13}$C (100 MHz, DMSO-d$_6$) δ, ppm: 7.57 s (cyclopropyl 2CH$_2$), 19.31 s (CH$_3$), 28.01 s (CH$_2$), 29.80 s (CH$_2$), 35.88 s (cyclopropyl CH), 49.32 s (piperazino 2CH$_2$), 52.06 s (piperazino 2CH$_2$), 56.48 s (CH$_2$), 57.26 s (CH$_2$), 106.38 d ($^4J_{C-F}$=2.7 Hz, C$_{ar}$), 108.18 s (C$_{ar}$), 110.91 d ($^2J_{C-F}$=23.1 Hz, C$_{ar}$), 118.56 d ($^3J_{C-F}$=7.8 Hz, C$_{ar}$), 129.95 s (C$_{pyr}$), 131.42 S (C$_{pyr}$), 139.16 S (C), 140.33 s (C), 145.13 d ($^2J_{C-F}$=10.1 Hz, C$_{ar}$ N), 146.01 s (C), 147.96 s (C), 150.07 s (C), 153.01 d ($^1J_{C-F}$=249.6 Hz, C$_{ar}$—F), 165.94 s (C(O) OH), 176.34 s (C=O).

MALDI-MS: [M+H]$^+$ 543.

Example 6. Preparation of 1-cyclopropyl-6-fluoro-7-(4-((2,8-dimethyl-4H-[1,3]dioxino-[4,5-c]pyridine-5-yl) methyl) piperazinyl)-4-oxo-1,4-dihydroquinolin-3-carboxylic acid (I-6)

Phase 1. Preparation of 5-hydroxymethyl-2,8-dimethyl-4H-[1,3]dioxino [4,5-c]pyridine (6)

Through suspension of 12.00 g (59.0 mmol) of pyridoxine hydrochloride (5) in 150 ml of acetaldehyde, while cooling to 3-5° C. and stirring, 39.00 g (1070.0 mmol) of hydrogen chloride are passed. The resulting reaction mixture is stirred for 20 hours The precipitate is filtered out, washed with ether and neutralized with an aqueous solution of potash. The product is filtered and recrystallized from ethyl alcohol. Yield is 5.65 g (50%), colorless crystals, melting temperature is 125° C. [RU02466728. *Fosfonievye soli na osnove proizvodnyh piridoksina* [Phosphonium salts based on pyridoxine derivatives]/Shtyrlin Y G., Shtyrlin N. V, Pugachev M V.—Publ.—Nov. 20, 2012].

Phase 2. Preparation of 5-bromomethyl-2,8-dimethyl-4H-[1,3]dioxino [4,5-c]pyridine (9)

1.34 g (5.1 mmol) of triphenylphosphine and 0.91 g (5.1 mmol) of bromosuccinimide are added to a solution of 0.99 g (5.1 mmol) of compound (6) in 20 ml of absolute chloroform at 20° C. After 1 h, the solution is concentrated in a vacuum and purified by column chromatography (eluent: diethyl ether:petroleum ether=2:1). Yield is 0.45 g (34%), light yellow oil-like substance.

NMR spectrum $^1$H (400 MHz, CDCl$_3$) δ, ppm: 1.57 d (3H, $^3J_{HH}$=5.1 Hz, CHCH$_3$), 2.40 s (31-1, CH$_3$), 4.27, 4.32 (AB-system, 2H, $^2J_{HH}$=−10.8 Hz, CH$_2$O), 4.94, 4.97 (AB-system, 2H, $^2J_{HH}$=−15.8 Hz, CH$_2$Br), 5.15 k (1H, $^3J_{HH}$=5.1 Hz, CHCH$_3$), 8.00 s (1H, CH).

NMR spectrum $^{13}$C (100 MHz, CDCl$_3$) δ, ppm.: 18.59 s (CH$_3$), 20.62 s (CH$_3$), 26.74 s (CH$_2$Br), 63.47 s (CH$_2$O), 97.32 s (CHCH$_3$), 126.79 s (C$_{pyr}$), 126.94 s (C$_{pyr}$), 140.91 s (C$_{pyr}$), 147.93 s (C$_{pyr}$), 148.63 s (C$_{pyr}$).

Phase 3. Preparation of 1-cyclopropyl-6-fluoro-7-(4-((2,8-dimethyl-4H-[1,3]dioxino-[4,5-c]pyridine-5-yl) methyl) piperazinyl)-4-oxo-1,4-dihydroquinolin-3-carboxylic acid (I-6)

0.41 g (1.2 mmol) of ciprofloxacin, 0.10 g (1.2 mmol) of sodium bicarbonate and 0.06 g (0.4 mmol) of potassium iodide are added successively to a solution of 0.38 g (1.5 mmol) of compound (9) in 30 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. Yield is 0.31 g (49%), light yellow crystals, melting temperature is 233° C. (decomp.).

NMR spectrum $^1$H (400 MHz, CDCl$_3$) δ, ppm: 1.17-1.20 m (2H, cyclopropyl CH$_2$), 1.33-1.38 m (2H, cyclopropyl CH$_2$), 1.58 d (3H, $^3J_{H-H}$=5.1 Hz, CH$_3$), 2.41 s (3H, CH$_3$), 2.61-2.63 m (4H, piperazino 2CH$_2$), 3.28-3.31 m (4H, piperazino 2CH$_2$), 3.43, 3.46 (AB-system, 2H, $^2J_{H-H}$=−13.4 Hz, CH$_2$N), 3.49-3.53 m (1H, cyclopropyl CH), 5.02, 5.08 (AB-system, 2H, $^2J_{H-H}$=−16.2 Hz, CH$_2$O), 5.18 k (1H, $^3J_{H-H}$=5.1 Hz, CH), 7.30 d (1H, $^4J_{H-F}$=7.0 Hz CH$_{ar}$), 7.89 d (1H, $^3J_{H-F}$=13.1 Hz, CH$_{ar}$), 7.92 s (1H, CH$_{ar}$), 8.67 s (1H, CH$_{pyr}$), 14.95 br s (1H, OH).

NMR spectrum $^{13}$C (100 MHz, CDCl$_3$) δ, ppm.: 8.30 s (cyclopropyl 2CH$_2$), 18.43 s (CH$_3$), 20.76 s (2CH$_3$), 35.39 s (cyclopropyl CH), 49.91 d ($^4J_{C-F}$=4.7 Hz, piperazino 2CH$_2$), 52.62 s (piperazino 2 CH$_2$), 57.59 s (CH$_2$), 64.49 s (CH$_2$), 97.21 s (CH CH$_3$), 104.92 s (C$_{ar}$), 108.09 s (C$_{ar}$), 112.34 d ($^2J_{C-F}$=23.5 Hz, C$_{ar}$), 119.78 d ($^3J_{C-F}$=7.8 Hz, C$_{ar}$), 126.82 s (C$_{pyr}$), 128.08 s (C$_{pyr}$), 139.13 s (C), 141.02 s (C), 145.88 d ($^2J_{C-F}$=10.4 Hz, C$_{ar}$—N), 147.26 s (C), 147.43 s (C), 148.02 s (C), 153.73 d ($^1J_{C-F}$=251.6 Hz, C$_{ar}$—F), 167.00 s (C(O) OH), 177.08 s (C=O). MALDI-MS: [M+H]$^+$ 509.

Example 7. Preparation of 1-cyclopropyl-6-fluoro-7-(4-((8-methyl-2-propyl-4H-[1,3]dioxino-[4,5-c]pyridine-5-yl) methyl) piperazinyl)-4-oxo-1,4-dihydroquinolin-3-carboxylic acid (I-7)

Phase 1. Preparation of 5-hydroxymethyl-8-methyl-2-propyl-4H-[1,3]dioxino [4,5-c]-pyridine (7)

In a round bottom flask equipped with a Dean-Stark nozzle, a suspension is prepared of 7.00 g (34.4 mmol) of pyridoxine hydrochloride (5), 13.70 g (72.1 mol) of p-toluenesulfonic acid monohydrate and 6.50 ml (72.2 mmol) of oily aldehyde in 120 ml of benzene. The reaction mass is boiled for 8 h, then the solvent is distilled off in a vacuum. The residue is neutralized to pH=7 with an aqueous solution of sodium bicarbonate. The precipitate is filtered and washed with benzene. Yield is 5.58 g (73%), white crystals, melting temperature is 101° C.

NMR spectrum $^1$H (400 MHz, CDCl$_3$) δ, ppm: 0.99 t (31-1, $^3J_{HH}$=7.4 Hz, CH$_3$CH$_2$CH$_2$), 1.52-1.58 m (2H, CH$_3$CH$_2$CH$_2$), 1.80-1.87 m (2H, CH$_3$CH$_2$CH$_2$), 2.34 s (3H, CH$_3$), 4.25 br s (1H, OH), 4.48 s (21-1, CH$_2$O), 4.96 s (2H, CH$_2$O), 4.97 t (1H, $^3J_{HH}$=4.8 Hz, CH), 7.83 s (1H, CH).

NMR spectrum $^{13}$C (100 MHz, CDCl$_3$) δ, ppm.: 14.01 s (C$_3$H$_7$), 17.08 s (C$_3$H$_7$), 18.17 s (CH$_3$), 36.41 s (C$_3$H$_7$), 60.04 s (CH$_2$O), 64.27 s (CH$_2$O), 99.97 s (CHC$_3$H$_7$), 127.76 s (C$_{pyr}$), 130.11 s (C$_{pyr}$), 139.17 s (C$_{pyr}$), 147.31 s (C$_{pyr}$), 147.99 s (C$_{pyr}$).

Phase 2. Preparation of 5-bromomethyl-8-methyl-2-propyl-4H-[1,3]dioxino [4,5-c]-pyridine (10)

3.49 g (13.3 mmol) of triphenylphosphine and 2.37 g (13.3 mmol) of bromosuccinimide are added to a solution of 2.97 g (13.3 mmol) of compound (7) in 20 ml of absolute chloroform at 20° C. After 1 h, the solution is concentrated in a vacuum and purified by column chromatography (eluent: diethyl ether:petroleum ether=2:1). Yield is 1.56 g (41%), white oil-like substance.

NMR spectrum $^1$H (400 MHz, CDCl$_3$) δ, ppm: 1.00 t (3H, $^3J_{HH}$=7.4 Hz, C$\underline{H}_3$CH$_2$CH$_2$), 1.52-1.62 m (2H, CH$_3$CH$_2$CH$_2$), 1.82-1.91 (2H, CH$_3$CH$_2$C$\underline{H}_2$), 2.43 s (3H, CH$_3$), 4.30, 4.34 (AB-system, 2H, $^2J_{HH}$=−10.8 Hz, CH$_2$O), 4.99 s (2H, CH$_2$Br), 5.03 t (1H, $^3J_{HH}$=5.2 Hz, C$\underline{H}$C$_3$H$_7$), 8.03 s (1H, CH).

NMR spectrum $^{13}$C (100 MHz, CDCl$_3$) δ, ppm: 14.02 s (C$_3$H$_7$), 17.07 s (C$_3$H$_7$), 18.49 s (CH$_3$), 26.73 s (C$_3$H$_7$), 36.35 s (CH$_2$Br), 63.63 s (CH$_2$O), 100.13 s (C$\underline{H}$C$_3$H$_7$), 127.00 s (C$_{pyr}$), 127.50 s (C$_{pyr}$), 140.36 s (C$_{pyr}$), 148.15 s (C$_{pyr}$), 148.61 s (C$_{pyr}$).

Phase 3. Preparation of 1-cyclopropyl-6-fluoro-7-(4-((8-methyl-2-propyl-4H-[1,3]dioxino-[4,5-c]pyridine-5-yl) methyl) piperazinyl)-4-oxo-1,4-dihydroquinolin-3-carboxylic acid (I-7)

1.44 g (4.4 mmol) of ciprofloxacin, 0.37 g (4.4 mmol) of sodium bicarbonate and 0.15 g (1.3 mmol) of potassium iodide are added successively to a solution of 1.51 g (5.3 mmol) of compound (10) in 30 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. Yield is 0.6 g (26%), light yellow crystals, melting temperature is 237-239° C.

NMR spectrum $^1$H (400 MHz, CDCl$_3$) δ, ppm: 0.99 t (3H, $^3J_{HH}$=7.4 Hz, C$_3$H$_7$), 1.13-1.19 m (2H, cyclopropyl CH$_2$), 1.34-1.37 m (2H, cyclopropyl CH$_2$), 1.49-1.60 m (2H, C$_3$H$_7$), 1.77-1.89 (2H, C$_3$H$_7$), 2.39 s (3H, CH$_3$), 2.60-2.62 m (4H, piperazino 2CH$_2$), 3.27-3.29 m (4H, piperazino 2CH$_2$), 3.41, 3.45 (AB-system, 2H, $^2J_{HH}$=−13.2 Hz, CH$_2$N), 3.52 m (1H, cyclopropyl CH), 5.00, 5.08 (AB-system, 2H, $^2J_{H-H}$=−16.2 Hz, CH$_2$O), 5.02 k (1H, $^3J_{H-H}$=5.2 Hz, CH), 7.29 d (1H, $^4J_{H-F}$=7.0 Hz, CH$_{ar}$), 7.84 d (1H, $^3J_{H-F}$=13.1 Hz, CH$_{ar}$), 7.90 s (1H, CH$_{ar}$), 8.63 s (1H, CH$_{pyr}$), 14.94 br s (1H, OH).

NMR spectrum $^{13}$C (100 MHz, CDCl$_3$) δ, ppm: 8.26 s (cyclopropyl 2CH$_2$), 13.99 s (C$_3$H$_7$), 17.07 s (C$_3$H$_7$), 18.29 s (CH$_3$), 35.39 s (C$_3$H$_7$), 36.43 s (cyclopropyl CH), 49.85 d ($^4J_{C-F}$=4.7 Hz, piperazino 2CH$_2$), 52.59 s (piperazino 2CH$_2$), 57.56 s (CH$_2$), 64.54 s (CH$_2$), 99.92 s (C$\underline{H}$C$_3$H$_7$), 104.90 d ($^4J_{C-F}$=2.9 Hz, C$_{ar}$), 107.96 s (C$_{ar}$), 112.20 d ($^2J_{C-F}$=23.4 Hz, C$_{ar}$), 119.63 d ($^3J_{C-F}$=7.8 Hz, C$_{ar}$), 126.89 s (C$_{pyr}$), 128.37 s (C$_{pyr}$), 139.09 s (C), 140.80 s (C), 145.84 d ($^2J_{C-F}$=10.3 Hz, C$_{ar}$—F), 147.19 s (C), 147.37 s (C), 148.07 s (C), 153.68 d ($^1J_{C-F}$=251.7 Hz, C—F), 166.95 s (C(O) OH), 176.99 s (C=O).

MALDI-MS: [M−H]$^+$ 535.

Example 8. Preparation of 1-cyclopropyl-6-fluoro-7-(4-((8-methyl-2-octyl-4H-[1,3]dioxino-[4,5-c]pyridine-5-yl) methyl) piperazinyl)-4-oxo-1,4-dihydroquinolin-3-carboxylic acid (I-8)

Phase 1. Preparation of 5-hydroxymethyl-2-octyl-8-methyl-4H-[1,3] dioxino [4,5-c]pyridine (8)

In a round bottom flask equipped with a Dean-Stark nozzle, a suspension is prepared of 7.00 g (34.4 mmol) of pyridoxine hydrochloride (5), 13.70 g (72.1 mol) of p-toluenesulfonic acid monohydrate and 5.90 ml (34.4 mmol) of nonyl aldehyde in 120 ml of benzene. The reaction mass is boiled for 8 h, then the solvent is distilled off in a vacuum. The residue is neutralized to pH=7 with an aqueous solution of sodium bicarbonate. The precipitate is filtered and washed with petroleum ether. Yield is 8.26 g (82%), white crystals, melting temperature is 175° C.

NMR spectrum $^1$H (400 MHz, CDCl$_3$) δ, ppm: 0.88 t (3H, $^3J_{HH}$=6.6 Hz, CH$_3$), 1.28-1.38 (10H, C$_8$H$_{17}$), 1.49-1.57 m (2H, C$_8$H$_{17}$), 1.80-1.94 m (2H, C$_8$H$_{17}$), 2.39 s (3H, CH$_3$), 3.30 br s (1H, OH), 4.53 s (2H, CH$_2$O), 4.99 s (2H, CH$_2$O), 5.00 k (1H, $^3J_{HH}$=5.2 Hz, CH), 7.83 s (1H, CH).

NMR spectrum $^{13}$C (100 MHz, CDCl$_3$) δ, ppm.: 14.25 s (C$_8$H$_{17}$), 18.33 s (CH$_3$), 22.80 s (C$_8$H$_{17}$), 23.71 s (C$_8$H$_{17}$), 29.35 s (C$_8$H$_{17}$), 29.51 s (C$_8$H$_{17}$), 29.60 s (C$_8$H$_{17}$), 31.99 s (C$_8$H$_{17}$), 34.42 s (C$_8$H$_{17}$), 60.38 s (CH$_2$O), 64.32 s (CH$_2$O), 100.21 s (C$\underline{H}$C$_8$H$_{17}$), 127.79 s (C$_{pyr}$), 129.81 s (C$_{pyr}$), 139.31 s (C$_{pyr}$), 147.59 s (C$_{pyr}$), 148.05 s (C$_{pyr}$).

Phase 2. Preparation of 5-bromomethyl-2-octyl-8-methyl-4H-[1,3]dioxino [4,5-c]pyridine (11)

2.67 g (10.2 mmol) of triphenylphosphine and 1.82 g (10.2 mmol) of bromosuccinimide are added to a solution of 2.99 g (10.2 mmol) of compound (8) in 20 ml of absolute chloroform at 20° C. After 1 h, the solution is concentrated in a vacuum and purified by column chromatography (eluent: diethyl ether:petroleum ether=2:1). Yield is 1.89 g (52%), white crystals, melting temperature is 175° C.

NMR spectrum $^1$H (400 MHz, CDCl$_3$) δ, ppm: 0.87 t (3H, $^3J_{HH}$=7.2 Hz, C$_8$H$_{17}$), 1.26-1.34 (10H, C$_8$H$_{17}$), 1.48-1.55 m (2H, C$_8$H$_{17}$), 1.79-1.93 m (2H, C$_8$H$_{17}$), 2.41 s (3H, CH$_3$), 4.28, 4.33 (AB-system, 2H, $^2J_{HH}$=−10.8 Hz CH$_2$O), 4.96 s (2H, CH$_2$Br), 4.99 t (1H, $^3J_{HH}$=5.2 Hz, C$\underline{H}$C$_8$H$_{17}$), 8.00 s (1H, CH).

NMR spectrum $^{13}$C (100 MHz, CDCl$_3$) δ, ppm.: 14.18 s (C$_8$H$_{17}$), 18.55 s (CH$_3$), 22.74 s (C$_8$H$_{17}$), 23.62 s (C$_8$H$_{17}$), 26.74 s (C$_8$H$_{17}$), 29.28 s (C$_8$H$_{17}$), 29.43 s (C$_8$H$_{17}$), 29.54 s (CH$_2$Br), 31.93 s (C$_8$H$_{17}$), 34.30 s (C$_8$H$_{17}$) 63.58 s (CH$_2$O), 100.26 s (C$\underline{H}$C$_8$H$_{17}$), 126.84 s (C$_{pyr}$), 127.21 s (C$_{pyr}$), 140.79 s (C$_{pyr}$), 148.05 s (C$_{pyr}$), 148.67 s (C$_{pyr}$).

Phase 3. Preparation of 1-cyclopropyl-6-fluoro-7-(4-((8-methyl-2-octyl-4H-[1,3]dioxino-[4,5-c]pyridine-5-yl) methyl) piperazinyl)-4-oxo-1,4-dihydroquinolin-3-carboxylic acid (I-8)

0.93 g (2.8 mmol) of ciprofloxacin, 0.24 g (2.8 mmol) of sodium bicarbonate and 0.10 g (0.8 mmol) of potassium iodide are added successively to a solution of 1.20 g (3.4 mmol) of compound (11) in 20 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. Yield is 0.91 g (54%), yellow crystals, melting temperature is 89-93° C.

NMR spectrum $^1$H (400 MHz, CDCl$_3$) δ, ppm: 0.86 t (3H, $^3J_{HH}$=6.8 Hz, C$_8$H$_{17}$), 1.15-1.18 m (2H, cyclopropyl CH$_2$), 1.23-1.38 m (12H, C$_8$H$_{17}$), 1.48-1.54 m (2H, cyclopropyl CH$_2$), 1.82-1.90 m (2H, C$_8$H$_{17}$), 2.41 s (3H, CH$_3$), 2.61-2.63 m (4H, piperazino 2CH$_2$), 3.29-3.33 m (4H, piperazino 2CH$_2$), 3.41, 3.45 (AB-system, 2H, $^2J_{H-H}$=−13.2 Hz, CH$_2$N), 3.52 m (1H, cyclopropyl CH), 5.01, 5.09 (AB-system, 2H, $^2J_{H-H}$=−16.2 Hz, CH$_2$O), 5.12 k (1H, $^3J_{H-H}$=5.2 Hz, CH), 7.30 d (1H, $^4J_{H-F}$=7.0 Hz, CH$_{ar}$), 7.88 d (1H, $^3J_{H-F}$=13.1 Hz, CH$_{ar}$), 7.91 s (1H, CH$_{ar}$), 8.66 s (1H, CH$_{pyr}$), 14.95 br s (1H, OH).

NMR spectrum $^{13}$C (100 MHz, CDCl$_3$) δ, ppm.: 8.29 s (cyclopropyl 2CH$_2$), 14.18 s (C$_8$H$_{17}$), 18.39 s (CH$_3$), 22.73 s (C$_8$H$_{17}$), 23.70 s (C$_8$H$_{17}$), 29.28 s (C$_8$H$_{17}$), 29.46 s (C$_8$H$_{17}$), 29.55 s (C$_8$H$_{17}$), 31.93 s (C$_8$H$_{17}$), 34.44 s (C$_8$H$_{17}$), 35.39 s (cyclopropyl CH), 49.90 d ($^4J_{C-F}$=4.6 Hz, piperazino 2CH$_2$), 52.62 s (piperazino 2CH$_2$), 57.60 s (CH$_2$), 64.58 s (CH$_2$), 100.13 s (CHC$_8$H$_{17}$), 104.89 d ($^4J_{C-F}$=2.9 Hz, C$_{ar}$), 108.06 s (C$_{ar}$), 112.32 d ($^2J_{C-F}$=23.4 Hz, C$_{ar}$), 119.75 d ($^3J_{C-F}$=7.7 Hz, C$_{ar}$), 126.82 s (C$_{pyr}$), 128.28 s (C$_{pyr}$), 139.12 s (C), 140.93 s (C), 145.88 d ($^2J_{C-F}$=10.3 Hz, C$_{ar}$—N), 147.30 s (C), 147.42 s (C), 148.08 s (C), 153.72 d ($^1J_{C-F}$=251.6 Hz, C$_{ar}$—F), 167.00 s (C(O) OH), 177.04 s (C=O).

MALDI-MS: [M–H]$^+$ 605.

Example 9. Preparation of hydrochloride of 1-cyclopropyl-6-fluoro-7-(4-((5-hydroxy-2,4-bis(hydroxymethyl)-6-methylpyridine-3-yl) methyl) piperazinyl)-4-oxo-1,4-dihydroquinolin-3-carboxylic acid (I-9)

To solution of 0.71 g (2.8 mmol) of compound (12) [M V. Pugachev, N V. Shtyrlin, E. V. Nikitina, L. P. Sysoeva, T. I. Abdullin, A. G. Iksanova, A. A. Ilaeva, E. A. Berdnikov, R. Z. Musin, Yu. G. Shtyrlin *Synthesis and antibacterial activity of novel phosphonium salts on the basis of pyridoxine/Bioorg. Med. Chem.*—2013. V. 21, Iss. 14.—P. 4388-4395] 0.79 g (2.4 mmol) of ciprofloxacin, 0.44 g (5.2 mmol) of sodium bicarbonate and 0.12 g (0.7 mmol) of potassium iodide are added successively to 20 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. After recrystallization, 15 ml of 0.1H of HCl solution are added and the solvent is distilled off in a vacuum. Yield is 0.84 g (65%), light yellow crystals, melting temperature is 190-195 (decomp.).

NMR spectrum $^1$H (400 MHz, DMSO-d$_6$) δ ppm: 1.15-1.19 br m (2H, cyclopropyl CH$_2$), 1.28-1.34 m (2H, cyclopropyl CH$_2$), 2.37 s (3H, CH$_3$), 2.66 br s (4H, piperazino 2CH$_2$), 3.27 br s (4H, piperazino 2CH$_2$), 3.30 s (2H, CH$_2$), 3.73 s (2H, CH$_2$), 3.79 m (1H, cyclopropyl CH), 4.56 S (2H, CH$_2$), 4.78 s (2H, CH$_2$), 6.00 br s (1H, OH), 7.54 d (1H, $^4J_{H-F}$=7.4 Hz, CH$_{ar}$), 7.87 d (1H, $^3J_{H-F}$=13.3 Hz, CH$_{ar}$), 8.64 s (1H, CHO, 9.15 br s (1H, OH).

NMR spectrum $^{13}$C (100 MHz, DMSO-d$_6$) δ, ppm: 7.48 s (cyclopropyl 2CH$_2$), 19.28 s (CH$_3$), 35.80 s (cyclopropyl CH), 49.44 d ($^4J_{C-F}$=4.6 Hz, piperazino 2CH$_2$), 51.60 s (piperazino 2CH$_2$), 53.41 s (CH$_2$), 56.17 s (CH$_2$), 63.26 s (CH$_2$), 106.49 s ($^4J_{C-F}$=3.1 Hz, C$_{ar}$), 106.72 s (C$_{ar}$), 110.85 d ($^2J_{C-F}$=23.0 Hz, C$_{ar}$), 118.68 d ($^3J_{C-F}$=7.7 Hz, C$_{ar}$), 127.72 s (C$_{pyr}$), 135.03 s (C$_{pyr}$), 139.08 s (C), 144.39 s (C), 144.95 d ($^2J_{C-F}$=10.2 Hz, C$_{ar}$—N), 147.91 s (C), 148.79 s (C), 149.44 s (C), 152.97 d ($^1J_{C-F}$=249.6 Hz, C$_{ar}$—F), 165.82 s (C(O) OH), 176.31 s (C=O).

MALDI-MS: [M+2H-Cl]$^+$ 514.

Example 10. Preparation of 1-cyclopropyl-6-fluoro-7-(4-((5-hydroxymethyl-2,2,8-trimethyl-4H-[1,3]dioxino [4,5-c]pyridine-6-yl) methyl) piperazinyl)-4-oxo-1,4-dihydroquinolin-3-carboxylic acid (I-10)

To solution of 1.30 g (4.3 mmol) of compound (13) [M V. Pugachev, N V. Shtyrlin, S. V. Sapognikov, L. P. Sysoeva, A. G. Iksanova, E. V. Nikitina, R. Z. Musin, O. A. Lodochnikova, E. A. Berdnikov, Yu. G. Shtyrlin *Bis-phosphonium salts of pyridoxine: the relationship between structure and antibacterial activity/Bioorg. Med. Chem.*—2013.—V. 21, Iss. 23.—P. 7330-7342] 1.29 g (3.9 mmol) of ciprofloxacin, 0.33 g (3.9 mmol) of sodium bicarbonate and 0.14 g (1.2 mmol) of potassium iodide are added successively to 20 ml of absolute DMFA at 20° C. After 4 h the solvent is removed in a vacuum. The dry residue is extracted with ethyl acetate, the insoluble part is filtered out, the filtrate is dried to dryness and recrystallized from a mixture of solvents acetone:water=2:1. Yield is 0.94 g (44%), light yellow crystals, melting temperature is 225° C. (decomp.).

NMR spectrum $^1$H (400 MHz, CDCl$_3$) δ, ppm: 1.16 br s (2H, cyclopropyl CH$_2$), 1.33 br s (2H, cyclopropyl CH$_2$), 1.54 s (6H, 2CH$_3$), 2.38 s (3H, CH$_3$), 2.79 br s (4H, piperazino 2CH$_2$), 3.29 br s (4H, piperazino 2CH$_2$), 3.49 br s (1H, cyclopropyl CH), 3.84 s (2H, CH$_2$N), 4.44 s (2H, CH$_2$O), 4.94 s (2H, CH$_2$O), 7.29 br s (1H, CH$_{ar}$), 7.89 d (1H, $^3J_{H-F}$=12.3 Hz, CH$_{ar}$), 8.67 S (1H, CH$_{ar}$), 14.93 br s (1H, OH).

NMR spectrum $^{13}$C (100 MHz, CDCl$_3$) δ, ppm.: 8.30 s (cyclopropyl 2CH$_2$), 18.39 s (CH$_3$), 24.79 s (2CH$_3$), 35.43 s (cyclopropyl CH), 49.63 s (piperazino 2CH$_2$), 52.27 s (piperazino 2 CH$_2$), 57.71 s (CH$_2$), 58.99 s (CH$_2$), 63.07 s (CH$_2$), 99.65 s (C(CH$_3$)$_2$), 105.20 s (C$_{ar}$), 108.09 S (C$_{ar}$), 112.39 d ($^2J_{C-F}$=23.4 Hz, C$_{ar}$), 120.08 d ($^3J_{C-F}$=7.7 Hz, C$_{ar}$), 125.65 s (C$_{pyr}$), 130.11 s (C$_{pyr}$), 139.05 s (C), 145.61 d ($^2J_{C-F}$=10.2 Hz, C$_{ar}$—N), 145.92 S (C), 146.08 S (C), 146.20 s (C), 147.54 s (C), 153.73 d ($^1J_{C-F}$=251.5 Hz, C$_{ar}$—F), 167.02 s (C(O) OH), 177.07 s (C=O).

MALDI-MS: [M+H]$^+$553.

Example 11. Preparation of hydrochloride of 1-cyclopropyl-6-fluoro-7-(4-((5-hydroxy-3,4-bis(hydroxymethyl)-6-methylpyridine-2-yl) methyl) piperazinyl)-4-oxo-1,4-dihydroquinolin-3-carboxylic acid (I-11)

0.91 g (1.7 mmol) of compound (I-10) and 1 ml of concentrated HCl in 20 ml of water are stirred for 24 h at 25° C. Then the solution is neutralized with sodium bicarbonate to pH=6. The precipitate is filtered out and washed successively with acetone, chloroform and water. After washing the precipitate, 17 ml of 0.1H of HCl solution are added and the solvent is distilled off in a vacuum. Yield is 0.69 g (76%), light yellow crystals, melting temperature is 212-215° C. (decomp.).

NMR spectrum $^1$H (400 MHz, DMSO-d$_6$) δ ppm: 1.18 br s (2H, cyclopropyl CH$_2$), 1.33 br s (2H, cyclopropyl CH$_2$), 2.44 s (3H, CH$_3$), 3.44 br s (4H, piperazino 2CH$_2$), 3.66 br s (414, piperazino 2CH$_2$), 3.84 br s (1H, cyclopropyl CH), 4.48 s (2H, CH$_2$), 4.62 s (21-1, CH$_2$O), 4.80 s (2H, CH$_2$O), 5.90 br s (1H, OH), 7.60 br s (1H, CH$_{ar}$), 7.91 d (1H, $^3J_{H-F}$=12.9 Hz, CH$_{ar}$), 8.65 s (1H, CH$_{ar}$), 9.69 br s (1H, OH), 15.10 br s (1H, OH).

NMR spectrum $^{13}$C (100 MHz, DMSO-d$_6$) δ, ppm: 7.62 s (cyclopropyl 2CH$_2$), 19.26 s (CH$_3$), 35.97 s (cyclopropyl CH), 46.60 s (piperazino 2CH$_2$), 51.15 s (piperazino 2CH$_2$), 55.92 s (CH$_2$), 56.03 s (CH$_2$), 57.27 s (CH$_2$), 106.80 s (C$_{ar}$), 111.13 d ($^2J_{C-F}$=23.6 Hz, C$_{ar}$), 119.18 d ($^3J_{C-F}$=7.7 Hz, C$_{ar}$), 133.50 S (C$_{pyr}$), 134.00 s (C$_{pyr}$), 139.05 s (C), 143.85 d ($^2J_{C-F}$=10.1 Hz, C$_{ar}$—N), 145.67 s (C), 148.08 s (C), 150.07 s (C), 152.81 d ($^1J_{C-F}$=249.5 Hz, C$_{ar}$—F), 165.81 s (C(O) OH), 176.32 s (C=O).

MALDI-MS: [M+H—Cl]$^+$ 513.

Example 12. Preparation of hydrochloride 1-cyclopropyl-6-fluoro-7-(4-((8-methyl-4H-[1,3]dioxino [4,5-c]pyridine-5-yl) methyl) piperazine-1-yl)-4-oxo-1,4-dihydroquinolin-3-carboxylic acid (I-12)

Phase 1. Preparation of 5-hydroxymethyl-8-methyl-4H-[1,3]dioxino [4,5-c]pyridine (14)

In a round bottom flask equipped with a Dean-Stark nozzle, a suspension is prepared of 20.00 g (97.0 mmol) of pyridoxine hydrochloride (5), 92.50 g (486.8 mol) of p-toluenesulfonic acid monohydrate and 5.84 g (194.6 mmol) of paraform in 150 ml of benzene. The reaction mass is boiled for 6 h, then the solvent is distilled off in a vacuum. A solution of 24.50 g (612.5 mmol) of sodium hydroxide in 150 ml of water is added to the mixture and neutralized to pH=7 with diluted hydrochloric acid. The product is extracted with ethyl acetate, which is then distilled off, and the dry residue is first washed with water and then with diethyl ether. Yield is 1.10 g (6%), crystalline substance of gray color. Melting temperature is 112-113° C.

NMR spectrum $^1$H (400 MHz, CDCl$_3$) δ, ppm: 2.36 s (311, CH$_3$), 4.09 br s (1H, OH), 4.49 s (2H, CH$_2$O), 4.96 s (2H, CH$_2$O), 5.26 s (2H, OCH$_2$O), 7.77 s (1H, CH).

NMR spectrum $^{13}$C (100 MHz, CDCl$_3$) δ, ppm: 18.21 s (CH$_3$), 59.97 s (CH$_2$O), 64.04 s (CH$_2$O), 91.20 s (OCH$_2$O), 128.17 S ($C_{pyr}$), 130.31 s ($C_{pyr}$), 139.43 s ($C_{pyr}$), 147.43 s ($C_{pyr}$), 147.58 s ($C_{pyr}$).

Phase 2. Preparation of 5-chloromethyl-8-methyl-4H-[1,3]dioxino [4,5-c]pyridine hydrochloride (15)

2.50 ml (34.4 mmol) of thionyl chloride are added to a solution of 1.00 g (5.5 mmol) of compound (14) in 20 ml of chloroform. The resulting reaction mixture is stirred at 20° C. for 3 hours. The solvent is removed in a vacuum. Quantitative yield, white crystalline substance, melting temperature is 190-192° C. (decomp.).

NMR spectrum $^1$H (400 MHz, DMSO-d6) δ, ppm: 2.54 s (3H, CH$_3$), 4.89 s (2H, CH$_2$O), 5.21 s (2H, CH$_2$O), 5.49 s (2H, OCH$_2$O), 8.43 s (1H, CH).

NMR spectrum $^{13}$C (100 MHz, DMSO-d6) δ, ppm: 14.76 s (CH$_3$), 39.03 s (CH$_2$Cl), 63.11 s (CH$_2$O), 91.72 s (OCH$_2$O), 130.46 S ($C_{pyr}$), 133.64 s ($C_{pyr}$), 135.52 s ($C_{pyr}$), 144.21 s ($C_{pyr}$), 148.92 S ($C_{pyr}$).

Phase 3. Preparation of hydrochloride 1-cyclopropyl-6-fluoro-7-(4-((8-methyl-4H-[1,3]dioxino [4,5-c]pyridine-5-yl) methyl) piperazine-1-yl)-4-oxo-1,4-dihydroquinolin-3-carboxylic acid (I-12)

0.63 g (1.9 mmol) of ciprofloxacin, 0.34 g (4.1 mmol) of sodium bicarbonate and 0.16 g (1.0 mmol) of potassium iodide are added successively to a solution of 0.50 g (2.1 mmol) of compound 15 in 20 ml of absolute DMFA at 20° C. The reaction mixture is stirred at 80° C. for 4 hours. The solvent is distilled off in a vacuum. The dry residue is extracted with ethyl acetate, the insoluble part is filtered out, the filtrate is dried to dryness and washed with acetone. To the resulting residue 6.4 ml of 0.1H of HCl solution are added and the solvent is distilled off in a vacuum. Yield is 0.34 g (34%), light yellow crystalline substance.

NMR spectrum $^1$H (400 MHz, DMSO-d6) δ, ppm: 1.18-1.22 m (2H, cyclopropyl CH$_2$), 1.36-1.41 m (2H, cyclopropyl CH$_2$), 2.44 s (3H, CH$_3$), 3.45-3.88 m (9H, piperazino 4CH$_2$+cyclopropyl CH), 4.41 s (2H, CH$_2$N), 5.41 s (2H, CH$_2$), 5.45 s (2H, CH$_2$), 7.60 d (1H, $^4J_{H-F}$=7.4 Hz, CH$_{ar}$), 7.96 d (1H, $^3J_{H-F}$=13.0 Hz, CH$_{ar}$), 8.66 s (1H, CH$_{ar}$), 8.68 s (1H, CH$_{pyr}$), 12.0 br s (1H, OH).

NMR spectrum $^{13}$C (100 MHz, DMSO-d6) δ, ppm: 7.61 s (cyclopropyl 2CH$_2$), 15.50 s (CH$_3$), 35.97 s (cyclopropyl CH), 46.12 s (piperazino 2CH$_2$), 50.53 s (piperazino 2CH$_2$), 51.58 s (CH$_2$), 64.28 s (CH$_2$), 91.33 s (CH$_2$), 106.86 s ($C_{ar}$), 106.91 s (C) 111.22 d ($^2J_{C-F}$=23.0 Hz, $C_{ar}$), 119.35 d ($^3J_{C-F}$=6.9 Hz, $C_{ar}$), 139.09 s (C), 148.25 s (C), 148.57 s (C), 153.83 d ($^1J_{C-F}$=249.4 Hz, $C_{ar}$— F), 165.83 s (C(O) OH), 176.39 s (C=O).

MALDI-MS: [M+H]$^+$ 496.

Example 13. The Study of the Antibacterial Activity of the Claimed Derivatives on the Basis of Ciprofloxacin Measurement of antibacterial activity was carried out on the strains of Staphylococcus aureus ATCC 29213 (museum strain), Staphylococcus epidermidis (clinical isolate), Micrococcus luteus (clinical isolate), Bacillus subtilis 168 (museum strain), Escherichia coli ATCC 25922 (museum strain), Salmonella typhimurium TA100 (museum strain), Pseudomonas aeruginosa ATCC 27853 (museum strain). A comparative assessment of the spectrum of antibacterial action on reference strains and clinical isolates of gram-positive microorganisms was carried out using a micromethod for determining the minimum inhibitory concentration (MIC) using serial dilutions in Mueller-Hinton broth using 96-well sterile plates.

The first lowest concentration of the antibiotic (from a series of successive dilutions), where bacterial growth is not visually determined, is considered to be the minimum inhibitory concentration (MIC).

For the preparation of inoculum (infectious material used for artificial contamination), intended for the study of antibacterial activity, was used a pure daily culture of bacteria grown on a dense nutrient medium (agar LB medium). In a sterile isotonic solution of sodium chloride, a suspension of microorganisms was prepared, adjusting the inoculum density to 0.5 according to the McFarland standard (1.5·10$^8$ CFU/ml). Then, the resulting inoculum was diluted to a concentration of 10$^7$ CFU/ml with LB-broth. The inoculum was used for 15 minutes after preparation; the purity of the bacterial strains was monitored before each experiment.

100 µl of Muller-Hinton broth was added to the wells of each plate; the test base was introduced into the first well at a concentration of 128 µg/ml in a volume of 100 µl and its concentration was adjusted to 0.25 µg/ml by consecutive two-fold dilution. Then, a prepared inoculum was added to each well, thereby diluting by half the concentration of the compounds under study (down to 64.0 µg/ml). Each preparation in the experiment was titrated three times. As a control, wells that did not contain the tested preparations were included (control of the growth of the culture). In addition, the purity of nutrient media and solvents was monitored. The plates were incubated in a thermostat at 360° C. for 24 hours.

The growth of cultures was assessed visually, comparing the growth of microorganisms in the presence of test compounds with the growth of culture without them.

The closest in chemical structure to the claimed antibacterial substances is ciprofloxacin, which was chosen as a prototype and comparison drug. Also as comparator drugs the applicant used "antibiotic of last resort" vancomycin and one of the most effective drugs of fluoroquinolone series—moxifloxacin.

As can be seen from the data presented in Table 1, almost all the claimed compounds have a pronounced antibacterial activity against the microorganism strains under study. At the same time, compounds I-2, I-3, I-9 and I-12 proved to be the most active; their antibacterial action with respect to gram-positive microorganisms turned out to be comparable with the comparison drugs.

TABLE 1

The values of the MIC of the claimed compounds (μg/ml) when the concentration of inoculum is $10^7$ CFU/ml

| Compound | Gram-positive bacteria | | | | Gram-negative bacteria | | |
|---|---|---|---|---|---|---|---|
| | M. luteus | B. $ subtilis | S. aureus | S. epidermidis | P. aerugenosa | E. coli | S. typhimurium |
| I-1 | 32 | <2 | 32 | 16 | >64 | 64 | 4 |
| I-2 | 4 | <2 | 2 | 2 | >64 | 2 | 2 |
| I-3 | 4 | <2 | 2 | 2 | >64 | 2 | 2 |
| I-4 | 8 | <2 | 16 | 32 | >64 | 64 | 4 |
| I-5 | 8 | <2 | 8 | 8 | 32 | 8 | 4 |
| I-6 | 8 | <2 | 8 | 8 | >64 | >64 | 4 |
| I-7 | 64 | <2 | 64 | 64 | >64 | >64 | 4 |
| I-8 | 64 | <2 | 32 | 64 | >64 | >64 | 4 |
| I-9 | 2 | 4 | 0.5 | 8 | >64 | 64 | 4 |
| I-10 | 8 | <2 | 8 | 8 | >64 | 64 | 4 |
| I-11 | 32 | <2 | 64 | 32 | >64 | 64 | 4 |
| I-12 | 16 | <2 | 1 | 0.5 | 32 | 8 | 0.5 |
| Moxifloxacin | 4 | <2 | 1 | 4 | 8 | 2 | 0.5 |
| Ciprofloxacin | 2 | <2 | 2 | 2 | 2 | 1 | 2 |
| Vancomycin | 4 | 64 | 4 | 4 | >64 | 64 | 64 |

For one of the most active compounds I-2, an in-depth study of antibacterial activity was conducted on clinical strains of microorganisms (*S. aureus* MRSA) presented in Table 2. Vancomycin, ciprofloxacin and ceftriaxone were used as comparator drugs.

TABLE 2

The values of the MIC for compounds I-2, as well as the comparator drugs in relation to gram-positive and gram-negative microorganisms (in μg/ml), when the concentration of inoculum is $10^7$ CFU/ml

| | The value of the MIC, μg/ml | | | |
|---|---|---|---|---|
| Strain | I-2 | Vancomycin | Ciprofloxacin | Ceftriaxon |
| | Gram-positive bacteria | | | |
| S. aureus MRSA 967 | 16 | 4 | 16 | >64 |
| S. aureus MRSA 981 | 16 | 2 | 32 | >64 |
| S. aureus MRSA 983 | 8 | 2 | 16 | >64 |
| S. aureus MRSA 1053 | 16 | 2 | 16 | >64 |
| S. aureus MRSA 1163 | 0.5 | 2 | 1 | >64 |
| S. aureus MRSA 1173 | 16 | 2 | 64 | >64 |
| S. aureus MRSA 1065 | 32 | 1 | 16 | >64 |
| S. aureus MRSA 1168 | 0.25 | 0.5 | 0.5 | 0.5 |
| S. aureus MRSA 2020 | 0.25 | 0.5 | 0.5 | 2 |
| S. aureus MRSA 1143 | 32 | 1 | 32 | >64 |
| S. aureus MRSA 1131 | 16 | 0.5 | 16 | >64 |
| S. aureus MRSA 1130 | 16 | 1 | 8 | >64 |

As can be seen from the data presented in Tables 1 and 2, the compounds showed comparable results to ciprofloxacin in terms of MIC with respect to gram-positive bacteria, and in the case of some strains, are superior to it. On clinical freshly isolated strains of *Staphylococcus aureus* MRSA in terms of MIC 1-2 in almost all cases is superior to ceftriaxone. In relation to gram-negative bacterial strains, compound I-2 exhibits low antibacterial activity.

Example 14. General Acute Toxicity Study of Compound I-2 in Mice after Intragastric Administration The acute toxicity of compound I-2 was studied using the fixed-dose method in ICR mice (CD-1) (6-8 weeks, 20-25 g) of both sexes, 6 animals per group. The starting dose for testing compound I-2 was 5000 mg/kg. The intragastric (oral) administration of compound I-2 to animals (<2.5 ml/100 g) using a gastric probe was used.

At a dose of 5000 mg/kg of compound I-2, mice of both sexes showed a slight inhibition of activity caused by mechanical effects on animals. After 20-30 minutes, the behavior of animals returned to normal. After 1.5-2 hours, the animals began to take food and water. During the whole experiment, the death of animals was not observed.

Throughout the experiment, all the main indicators of vital activity in experimental animals corresponded to the norm and did not differ from the control ones. The mice had a good appetite, shiny coat, visible mucous membranes were pale pink in color, the behavior corresponded to this species of animal, no abnormalities were observed during the observation period.

TABLE 3

Acute toxicity of compound I-2

| Animal species | Sex | Dose, mg/kg | Number of animals in the group/ number of dead animals | $LD_{10}$ | $LD_{16}$ | $LD_{50}$ with confidence interval | $LD_{84}$ |
|---|---|---|---|---|---|---|---|
| mouse | males | 5000 | 6/0 | >5000 | >5000 | >5000 | >5000 |
| | females | 5000 | 6/0 | >5000 | >5000 | >5000 | >5000 |

At the end of the experiment, euthanasia and pathomorphological dissection of control and experimental animals were performed. No changes were observed during the autopsy of mice. Control and experimental animals did not differ from each other At necropsy of dead mice treated with compound I-2 intragastrically, the following picture was observed. Corpses of animals are of the correct constitution, average fatness. Natural openings: the mouth is closed, the tongue is in the mouth, the mucous membrane of the lips and the gums are pale pink, smooth and shiny. Nasal openings—mucous membrane is pale pink, dry, no efflux, permeability is good. Ear shells are unchanged; the external auditory canal is clean. Anus is closed, mucous membrane is pale pink. The hair is kept well, the fleece is shiny. The skin is elastic, the subcutaneous fiber is well expressed, has yellowish color and is elastic. The muscles are reddish, well developed, tendons and ligaments are white, elastic and durable. The configuration of bones and joints is not broken. The position of the organs of the thoracic and abdominal cavities: anatomically correct. There is no fluid in the thoracic and abdominal cavities. The patency of the pharynx and esophagus is not broken. The heart is not changed in volume. The cavities of the heart contain a small amount of non-clotted blood, the endocardium is smooth and shiny. Lungs are from pale pink to red, unevenly colored, lobulation is well expressed. The spleen is not enlarged, with sharp edges, oblong in shape, has elastic consistency, red-brown in color. The liver is not enlarged, with sharp edges, the shape is not changed, the consistency is dense, the color is cherry. The stomach contains a gray feed mass of a uniform consistency. The mucous membrane of the stomach is pale gray. The mucous membrane of the thin and thick parts of the intestine is of pale pink or pale gray color. The kidneys are bean-shaped, dark brown in color, in the paranephric body there is a moderate amount of fat, the capsule is easily separated, the boundary between the cortical and brain zones is expressed. The urinary bladder is empty or filled up with urine of light yellow color, the mucous membrane is of pale pink color. Genitals are without abnormalities. Males' testicles are of elastic consistency, are in the cavity of the scrotum, have an elliptical shape. The females have normal ovaries and uterus. The brain is not edematic, the brain matter is elastic, without hemorrhages.

The mean lethal dose for compound I-2 was not detected in mice, because mortality was not observed with the administration of compound I-2 at a dose of 5000 mg/kg. Thus, studies have shown that compound I-2 belongs to hazard class 4, to low-hazard substances.

Thus, new fluoroquinolones based on ciprofloxacin, which have high antibacterial activity and low toxicity, have been obtained.

The claimed invention meets the criterion of "novelty" applied to the inventions, as the studied level of technology did not identify technical solutions that have the stated set of distinctive features that ensure the achievement of the stated results.

The claimed invention meets the criterion of "inventive step" applied to the inventions, as it is not obvious to a person skilled in this field of science and technology.

The claimed invention meets the criterion of "industrial applicability", as it can be implemented at any specialized enterprise using standard equipment, well-known domestic materials and technologies.

What is claimed is:

1. A derivative of ciprofloxacin of general formula (I)

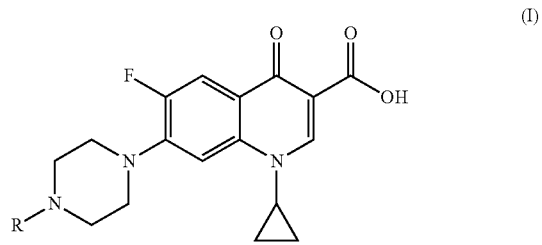

where R=

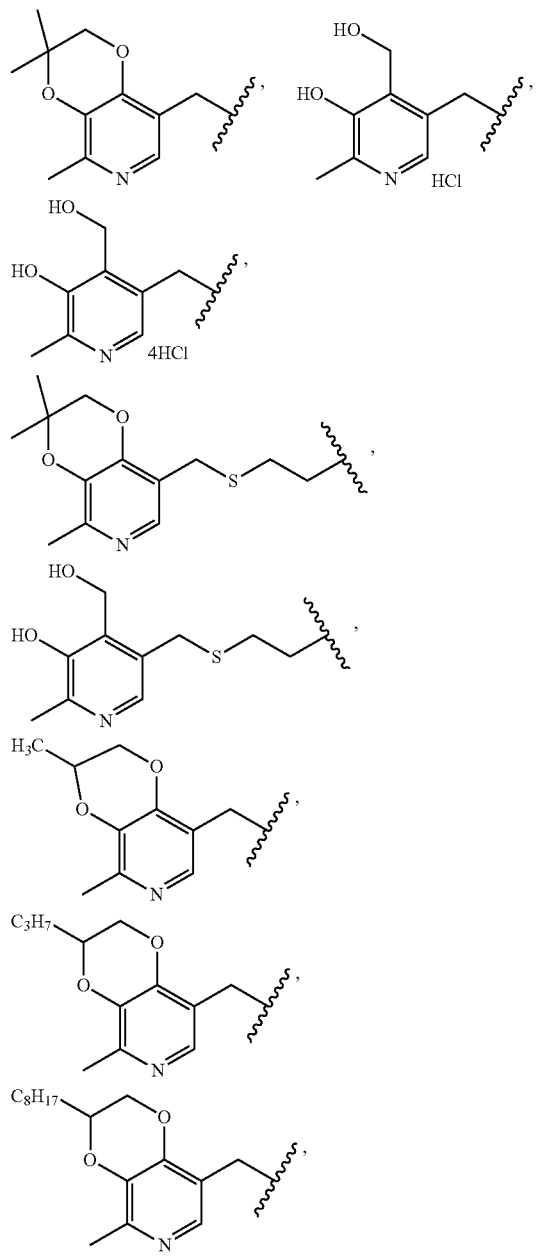

-continued
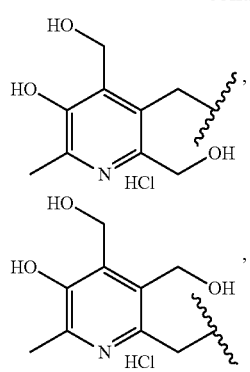
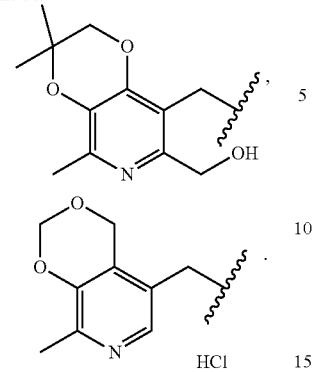
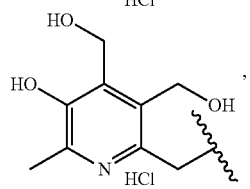
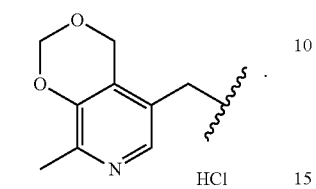
* * * * *

UNITED STATES PATENT AND TRADEMARK OFFICE
CERTIFICATE OF CORRECTION

PATENT NO. : 10,759,810 B2  
APPLICATION NO. : 16/397860  
DATED : September 1, 2020  
INVENTOR(S) : Yurij G. Shtyrlin et al.

Page 1 of 1

It is certified that error appears in the above-identified patent and that said Letters Patent is hereby corrected as shown below:

On the Title Page

Item (72), Inventors, change the name of the 4th Inventor from: Roman S. Pavel'Ev to: Roman S. Pavel'ev; and the address of the 7th Inventor from: Kaliningrad Obl. to: pos. Donskoe Kaliningrad Obl.

Signed and Sealed this
Twelfth Day of January, 2021

Andrei Iancu
*Director of the United States Patent and Trademark Office*